US009115407B2

(12) United States Patent
Cangelosi et al.

(10) Patent No.: US 9,115,407 B2
(45) Date of Patent: Aug. 25, 2015

(54) RATIOMETRIC PRE-RRNA ANALYSIS

(75) Inventors: Gerard A. Cangelosi, Seattle, WA (US);
John Scott Meschke, Bothell, WA (US);
Kris Weigel, Seattle, WA (US)

(73) Assignees: University of Washington, Seattle, WA (US); Seattle Biomedical Research Institute, Seattle, WA (US)

( * ) Notice: Subject to any disclaimer, the term of this patent is extended or adjusted under 35 U.S.C. 154(b) by 0 days.

(21) Appl. No.: 13/133,889

(22) PCT Filed: Dec. 10, 2009

(86) PCT No.: PCT/US2009/067565
§ 371 (c)(1),
(2), (4) Date: Nov. 1, 2011

(87) PCT Pub. No.: WO2010/068802
PCT Pub. Date: Jun. 17, 2010

(65) Prior Publication Data
US 2012/0094285 A1    Apr. 19, 2012

Related U.S. Application Data

(60) Provisional application No. 61/121,485, filed on Dec. 10, 2008.

(51) Int. Cl.
| | | |
|---|---|---|
| C12Q 1/68 | (2006.01) | |
| C12P 19/34 | (2006.01) | |
| C07H 21/02 | (2006.01) | |
| C07H 21/04 | (2006.01) | |
| C12Q 1/02 | (2006.01) | |

(52) U.S. Cl.
CPC . C12Q 1/689 (2013.01); C12Q 1/02 (2013.01)

(58) Field of Classification Search
USPC .............. 435/6.1, 6.11, 6.12, 91.1, 91.2, 183, 435/6.15; 436/94, 501; 536/23.1, 24.3, 536/24.33, 25.3
See application file for complete search history.

(56) References Cited

U.S. PATENT DOCUMENTS

| | | | |
|---|---|---|---|
| 5,712,095 | A | 1/1998 | Britschgi et al. |
| 6,057,096 | A | 5/2000 | Rothschild et al. |
| 7,608,399 | B2 | 10/2009 | Reed et al. |
| 2004/0019269 | A1 | 1/2004 | Schaffer et al. |
| 2004/0265934 | A1 | 12/2004 | Stender et al. |
| 2005/0048463 | A1* | 3/2005 | Deng et al. .................. 435/4 |
| 2005/0142575 | A1 | 6/2005 | Jannes et al. |
| 2006/0057669 | A1* | 3/2006 | Grummt et al. .............. 435/69.1 |
| 2007/0117770 | A1 | 5/2007 | Drygin et al. |
| 2008/0009011 | A1 | 1/2008 | Stroot et al. |
| 2008/0167353 | A1* | 7/2008 | Yeo et al. ...................... 514/364 |
| 2008/0261206 | A1 | 10/2008 | Kim et al. |

FOREIGN PATENT DOCUMENTS

| | | |
|---|---|---|
| EP | 0446972 | 9/1991 |
| JP | 07/8294 | 1/1995 |
| JP | 2008/051821 | 3/2008 |
| WO | WO 2010/068802 | 6/2010 |

OTHER PUBLICATIONS

Cangelosi et al., Molecular Detection of Viable Bacterial Pathogens in Water by Ratiometric Pre-rRNA Analysis. Applied and Environment Microbiology, 76, 960-962, 2010.*
Notification of the International Search Report and the Written Opinion of the International Searching Authority issued Mar. 9, 2010 in International Application No. PCT/US2009/067565.
Notification Concerning the Transmittal of the International Preliminary Report on Patentability issued Jun. 23, 2011 in International Application No. PCT/US2009/067565, now WO 2010/068802.
Rantsiou, et al., "Detection, Quantification and Vitality of Listeria Monocytogenes in Food as Determined by Quantitative PCR." International Journal of Food Microbiology, Jan. 15, 2008, vol. 121, Issue 1, p. 99-105.
Weber, et al. "Oligonucleotide Microarrays for the Detection and Identification of Viable Beer Spoilage Bacteria." Journal of Applied Microbiology, Oct. 2008, vol. 105, Issue 4, p. 951-962.
U.S. Appl. No. 11/880,790, filed Jan. 29, 2009, Reed, et al.
Cangelosi, et al. "Depletion of Pre-16s rRNA in Starved *Escherichia coli* Cells." J.Bacteriol. 1997; 179:4457-4463.
Cangelosi, et al., "Detection of Rifampin- and Ciprofloxacin-Resistant Mycobacterium Tuberculosis by Using Species-Specific Assays for Precursor rRNA." Antimicrob.Agents Chemother. 1996; 40:1790-1795.
Gedalanga, et al. "Development of a Quantivative PCR Method to Differentiate Between Viable and Nonviable Bacteria in Environmental Water Samples." Appl Microbiol Biotechnol. 209; 82:587-596.
Gill, et al. "Nucleic Acid Isothermal Amplification Technologies—A Review." Nucleosides, Nucleotides, and Nucleic Acids. 2008; 27:224-243.
Heffner, et al. "Multilevel Likelihood Ratios for Identifying Exudative Pleural Effusions." Chest. Jun. 2002, vol. 121, No. 6, p. 1916-1920.
Nolan, et al. "Quantification of mRNA Using Real-Time RT-PCR." Nature Protocols 2006; 1: 1559-1582.
Varma, et al. "An Outbreak of *Escherichia coli* O157 Infection Folloing Exposure to a Contaminated Building." JAMA., Nov. 26, 2003, vol. 290, No. 20, p. 2709-2712.
Aellen, S., et al., "Detection of Live and Antibiotic-Killed Bacteria by Quantitative Real-Time PCR of Specific Fragments of rRNA," Antimicrobial Agents and Chemotherapy, vol. 50, No. 6, pp. 1913-1920, (2006).
Menendez, M., et al., "Analysis of the Precursor rRNA Fractions of Rapidly Growing Mycobacteria: Quantification by Methods that Include the Use of a Promoter (rrnA P1) as a Novel Standard," Journal of Bacteriology, vol. 187, No. 2, pp. 534-543, (2005).

(Continued)

*Primary Examiner* — Frank Lu
(74) *Attorney, Agent, or Firm* — Stoel Rives, LLP; Zhi-Xiang (Alex) Oh

(57) ABSTRACT

Disclosed are compositions and methods for detecting the presence of viable cells in a sample. Included are compositions and methods for increasing the sensitivity of a nucleic acid amplification test for determining the presence of at least one target microorganism in a sample. Also disclosed are compositions and methods for detecting ribosomal RNA precursors (pre-rRNA) as dynamic indicators of viable microorganisms in a sample.

23 Claims, 14 Drawing Sheets

(56) References Cited

OTHER PUBLICATIONS

Oerther, D., et al., "Monitoring Precursor 16S rRNAs of Acinetobacter spp. in Activated Sludge Wastewater Treatment Systems," Applied and Environmental Microbiology, vol. 66, No. 5, pp. 2154-2165, (2000).

O'Grady, J., et al., "Rapid Detection of Listeria monocytogenes in food using culture enrichment combined with real-time PCR," Food Microbiology, vol. 26, pp. 4-7, (2008).

Stroot, P.G., et al., "Elevated Precursor 16S rRNA Levels Suggest the Presence of Growth Inhibitors in Wastewater," Water Science and Technology, vol. 47, No. 11, pp. 241-250, (2003).

Oerther, et al., "Using Ribosome Genesis as a Sensitive Indicator of Microbial Viability to Test Disinfection Efficacy," American Water Works Association—Water Quality Technology Conference, pp. 1-8, 2003.

EP Communication issued Jun. 3, 2014 in European Patent Application No. 09832566.5.

Supplemental European Search Report issued Nov. 30, 2012 in European Patent Application No. 09832566.5.

EP Communication issued Dec. 18, 2012 in European Patent Application No. 09832566.5.

Response to EP Communication issued Nov. 30, 2012 and Dec. 18, 2012 filed Jun. 27, 2013 in European Patent Application No. 09832566.5.

Response to EP Communication issued Jun. 3, 2014 filed Sep. 30, 2014 in European Patent Application No. 09832566.5.

Luz, et al., "Variation of the Ribosomal Operon 16S-23S Gene Spacer Region in Representatives of *Salmonella enterica* Subspecies," Journal of Bacteriology, vol. 180, No. 8, pp. 2144-2131, (1998).

Iskakova, et al., "Chapter 11. Regulation of Ribosome Biosynthesis in *Escherichia coli*," Protein Synthesis and Ribosome Structure, Edited by Knud H. Nierhaus, Daniel Wilson, John Wiley & Sons, pp. 429-431, (2004).

\* cited by examiner

| Genera (gram status +/-) | Example Species |
|---|---|
| *Acinetobacter* (-) | *Acinetobacter baumanii* |
| *Actinobacillus* (-) | *Actinobacillus actinomycetemcomitans*\* |
| *Aeromonas* (-) | *Aeromonas caviae* |
| | *Aeromonas hydrophila* |
| | *Aeromonas veronii biovar sobria* |
| *Arcobacter* (-) | |
| *Bacteroides* (-) | *Bacteroides fragilis* |
| *Bordetella* (-) | *Bordetella bronchiseptica* |
| | *Bordetella parapertussis* |
| | *Bordetella pertussis* |
| *Borrelia* (-) | *Borrelia burgdorferi* |
| | *Borrelia recurrentis* |
| *Brucella* (-) | *Brucella abortus* |
| | *Brucella canis* |
| | *Brucella melintensis* |
| | *Brucella suis* |
| *Burkholderia* (-) | *Burkholderia cepacia* |
| | *Burkholderia mallei* |
| | *Burkholderia pseudomallei* |

FIG. 6

| | |
|---|---|
| *Campylobacter* (-) | *Campylobacter coli* |
| | *Campylobacter fetus* |
| | *Campylobacter jejuni* |
| | *Campylobacter lari* |
| *Citrobacter* (-) | *Citrobacter diversus* |
| | *Citrobacter freundii* |
| *Cronobacter* (-) | *Cronobacter sakazakii* |
| *Edwardsiella* (-) | *Edwardsiella tarda* |
| *Enterobacter* (-) | *Enterobacter aerogenes* |
| | *Enterobacter agglomerans* |
| | *Enterobacter cloacae* |
| *Escherichia* (-) | *Escherichia coli* |
| | EaggEC = enteroaggregative E. coli |
| | EHEC = enterohemorrhagic E. coli |
| | EIEC = enteroinvasive E. coli |
| | EPEC = enteropathogenic E. coli |
| | ETEC = enterotoxigenic E. coli |
| | Opportunistic Escherichia coli |
| | UPEC = uropathogenic E. coli |
| *Eubacterium* (-) | |
| *Francisella* (-) | *Francisella tularensis* |
| *Fusobacterium* (-) | |

FIG. 6 cont.

| | |
|---|---|
| *Haemophilus* (-) | *Haemophilus aegyptius* |
| | *Haemophilus ducreyi* |
| | *Haemophilus haemolyticus* |
| | *Haemophilus influenzae* |
| | *Haemophilus parahaemolyticus* |
| | *Haemophilus parainfluenzae* |
| *Helicobacter* (-) | *Helicobacter cinaedi* |
| | *Helicobacter fennelliae* |
| | *Helicobacter pylori* |
| *Klebsiella* (-) | *Klebsiella oxytoca* |
| | *Klebsiella pneumoniae* |
| *Legionella* (-) | *Legionella pneumophila* |
| *Leptospira* (-) | *Leptospira interrogans* |
| | *Leptospira interrogans serogroup canicola* |
| | *Leptospira interrogans serogroup icterohaemorrhagiae* |
| | *Leptospira interrogans serogroup pomona* |
| *Moraxella* (-) | *Moraxella catarrhalis* |
| *Morganella* (-) | *Morganella morganii* |
| *Neisseria* (-) | *Neisseria gonorrhoeae* |
| | *Neisseria meningitides* |
| *Pasteurella* (-) | *Pasteurella multocida* |

FIG. 6 cont.

| | |
|---|---|
| *Plesiomonas* (-) | *Plesiomonas shigelloides* |
| *Porphyromonas* (-) | *Porphyromonas gingivalis* |
| *Prevotella* (-) | |
| *Proteus* (-) | *Proteus mirabilis* |
| | *Proteus vulgaris* |
| *Providencia* (-) | *Providencia alcalifaciens* |
| | *Providencia rettgeri* |
| | *Providencia stuartii* |
| *Pseudomonas* (-) | *Pseudomonas aeruginosa* |
| *Salmonella* (-) | *Salmonella enterica* |
| | *Salmonella cholerasuis* |
| | *Salmonella enteritidis* |
| | *Salmonella paratyphi* |
| | *Salmonella typhi* |
| | *Salmonella typhimurium* |
| *Serratia* (-) | *Serratia liquifaciens* |
| | *Serratia marcesans* |
| *Shigella* (-) | *Shigella boydii* |
| | *Shigella dysenteriae* |
| | *Shigella flexneri* |
| | *Shigella sonnei* |

FIG. 6 cont.

| | |
|---|---|
| Stenotrophomonas (-) | Stenotrophomonas maltophilia |
| Treponema (-) | Treponema carateum |
| | Treponema denticola |
| | Treponema pallidum |
| Veillonella (-) | |
| Vibrio (-) | Vibrio alginolyticus |
| | Vibrio cholerae |
| | Vibrio damsela |
| | Vibrio fluvialis |
| | Vibrio furnisii |
| | Vibrio hollisae |
| | Vibrio metchnikovii |
| | Vibrio mimicus |
| | Vibrio parahaemolyticus |
| | Vibrio vulnificus |
| Yersinia (-) | Yersinia enterocolitica |
| | Yersinia pestis |
| | Yersinia pseudotuberculosis |
| Actinomyces (+) | Actinomyces israelii |
| | Actinomyces naeslundii |

FIG. 6 cont.

| | |
|---|---|
| *Bacillus* (+) | *Bacillus anthracis* |
| | *Bacillus cereus* |
| | *Bacillus stearothermophilus* |
| | *Bacillus subtilis* |
| | *Bacillus thuringiensis* |
| *Bifidobacterium* (+) | |
| *Clostridium* (+) | *Clostridium botulinum* |
| | *Clostridium difficile* |
| | *Clostridium perfringens* |
| *Corynebacterium* (+) | *Corynebacterium diphtheriae* |
| | *Corynebacterium jeikeum* |
| | *Corynebacterium urealyticum* |
| *Enterococcus* (+) | *Enterococcus faecalis* |
| | *Enterococcus faecium* |
| *Lactobacillus* (+) | |
| *Listeria* (+) | *Listeria monocytogenes* |
| *Micrococcus* (+) | |
| *Mobiluncus* (+) | |
| *Mycobacterium* (+) | *Mycobacterium avium complex* |
| | *Mycobacterium kansasii* |
| | *Mycobacterium leprae* |

FIG. 6 cont.

| | |
|---|---|
| | *Mycobacterium marinum* |
| | *Mycobacterium tuberculosis* |
| | *Mycobacterium ulcerans* |
| | *Other slowly-growing non-tuberculous mycobacteria* |
| | *Rapidly-growing non-tuberculous mycobacteria* |
| Nocardia (+) | *Nocardia asteroides* |
| | *Nocardia brasiliensis* |
| Peptostreptococcus (+) | |
| Propionibacterium (+) | *Propionibacterium acnes* |
| Rhodococcus (+) | |
| Staphylococcus (+) | *Staphylococcus aureus* |
| | *Staphylococcus epidermidis* |
| | *Staphylococcus saprophyticus* |
| Streptococcus (+) | *Streptococcus agalactiae* |
| | *Streptococcus anginosus* |
| | *Streptococcus bovis* |
| | *Streptococcus equismilis* |
| | *Streptococcus pneumoniae* |
| | *Streptococcus pyogenes* |
| | *Viridans streptococci including Streptococcus mutans* |
| Streptomyces (+) | |

FIG. 6 cont.

| Target Microorganism | Forward Primer 1 | Reverse Primer 1 | Forward Primer 2 | Reverse Primer 2 | Reverse Transcriptase Primer 1 | Reverse Transcriptase Primer 2 | Reverse Transcriptase Primer 3 |
|---|---|---|---|---|---|---|---|
| Mycobacterium avium complex | TTGGCCATACCTAGCACTCC (SEQ ID NO: 1) | GATTGCCCACGTGTTACTCA (SEQ ID NO: 2) | | | GCCCGCACGCTCACAGTTAAG (SEQ ID NO: 3) | | |
| Aeromonas hydrophila | ATTCAGCCGCCTTAACAGC (SEQ ID NO: 4) | AACTGTTATCCCCCTCGAC (SEQ ID NO: 5) | | | CTACAAGACTCTAGCTGGACAGT (SEQ ID NO: 6) | | |
| Bacillus anthracis | ACAAACAACGTGAAACGTCAAT (SEQ ID NO: 7) | GTCCGCGGCTAACTTCATAA (SEQ ID NO: 8) | AACTTTATTGGAGAGTTTGATCCTG (SEQ ID NO: 9) | CCCGGAGTTATCCCAGTCTT (SEQ ID NO: 10) | CAGTTTCCAATGACCCTCCA (SEQ ID NO: 11) | TGCACTCAAGTCTCCCAGTTT (SEQ ID NO: 12) | GAGCCGTTACCTCACCAACT (SEQ ID NO: 13) |
| Bordetella pertussis | GATCAGGGTCCACACACAGA (SEQ ID NO: 14) | CCACGCTTCGCGTAGTTAT (SEQ NO: 15) | AAGCGATACGGATCCTGGTT (SEQ ID NO: 16) | CCGACTTGCATGTGTAAAGC (SEQ NO: 17) | GCCCGGTAGTTAAAAATGDAG (SEQ NO: 18) | AAGGTTAAGCCCTGGGATTTC (SEQ NO: 19) | TCCTCTCAAACCAGCTACGG (SEQ NO: 20) |
| Borrelia burgdorferi | GCCAAAAGAATAAACAAAACTG (SEQ NO: 21) | CCGTTTGACTTGCATGCTTA (SEQ NO: 22) | TTGGAAGATGAGAGAAGCGAAG (SEQ NO: 23) | TTCGCCACTGAATGTATTGC (SEQ NO: 24) | AGTTTCCAACATAGGTCCACA (SEQ NO: 25) | AGTTGAGCGTGTGGTATTTTATGC (SEQ NO: 26) | TGCCTTGGTAGGCATTTACC (SEQ NO: 27) |
| Campylobacter jejuni | TTTTAGGCATAAGCAATTATGTAAAATC (SEQ NO: 28) | CGTTCACTCTGAGCCAGGAT (SEQ NO: 29) | GATTTAGGCATAAGCAATTATGTAAA (SEQ NO: 30) | AGCCAGGATCAAACTCTCCA (SEQ NO: 31) | GAGACTTGATAATCGGCCTACG (SEQ NO: 32) | CCTACGCGCCCTTTACG (SEQ NO: 33) | TCGTTTCCAACTGTTGTCCT (SEQ NO: 34) |
| Clostridium difficile | AAGAAACAAACCATAAAGCCAGA (SEQ NO: 35) | TCGCTCAACTTGCATGTGTT (SEQ NO: 36) | TTTGATAACAATAGTATCTGAGCCTGA (SEQ NO: 37) | GGTAGGTTACCCACGCGGTTA (SEQ NO: 38) | TCCACTCTCCTCTCCTGCAC (SEQ NO: 39) | TGCACTCAAGTCTCCCAGTTT (SEQ NO: 40) | CGTAGGAGTTTGGACCGTGT (SEQ NO: 41) |
| Escherichia coli | GTCGCAAGACGAAAAATGAA (SEQ NO: 42) | TCGACTTGCATGTGTTAGGC (SEQ NO: 43) | TCTTTGAGCATCAAACTTTTAAATTG (SEQ NO: 44) | CAGGCAGTTTCCCAGACATT (SEQ NO: 45) | TCAGATGCAGTTCCCAGGTT (SEQ NO: 46) | CCCGGGATTTCACATCT (SEQ NO: 47) | CTCAGACCAGCTAGGGATCG (SEQ NO: 48) |
| Haemophilus influenzae | CGATTGAACTTGAATTGAAGAGTT (SEQ NO: 49) | CACTCCTCAGCAAGAAAACCA (SEQ NO: 50) | TTGAAGTCTTAATAGGTGCTTAACTGA (SEQ NO: 51) | CTTTCTCCTGCTACCGTTCG (SEQ NO: 52) | CTGAAATGCAATTCCCAGGT (SEQ NO: 53) | GGGCTTCACACCTCACT (SEQ NO: 54) | CAGTCCCGCACTTTCATCTT (SEQ NO: 55) |
| Helicobacter pylori | GTTGTTAGGAATAACAAC (SEQ NO: 56) | AGCTTCATCGTTCGACTTGC (SEQ NO: 57) | CGAGTTCTTGTGATACGCTAAA (SEQ NO: 58) | TTCCAATGGCTATCCCAAAC (SEQ NO: 59) | CTCCCACACTCTAGAATAGTAGT (SEQ NO: 60) | ACAACTCTAGAATAGTAGTTTCAAATG (SEQ NO: 61) | |
| Legionella pneumophila | AGAGCTAGTGCCGGAATTGA (SEQ NO: 62) | TGAGTTCCCCAAGTTGTCC (SEQ NO: 63) | GACAAACTGTGTGGGCACTTT (SEQ NO: 64) | GCTAGACAATGCTGCCGTTC (SEQ NO: 65) | AGGTTAAGCCCAGGAATTCA (SEQ NO: 66) | ATTATCTGACCGTCCCAGGTT (SEQ NO: 67) | GTCCCCAGCTTTCGTCCT (SEQ NO: 68) |
| Listeria monocytogenes | AGCTGTTTTCAACAAAACAAACTA (SEQ NO: 69) | CCTGAGCCAGGATCAAACTC (SEQ NO: 70) | GCTGTTTTCAACAAAACAAACTAGTAA (SEQ NO: 71) | AGCAAGCTGTTCCTCCGTTC (SEQ NO: 72) | GGGGCTTTCACATCAGACTT (SEQ NO: 73) | AATGACCCTCCCCGGTTA (SEQ NO: 74) | AGGTTGCCACGTGTTACTC (SEQ NO: 75) |

FIG. 7

| Mycobacterium tuberculosis | TTTCCAAAGGGAGTGTTTGG (SEQ NO 76) | ACCCAGTTTCCCAGGCTTAT (SEQ NO: 77) | TACCTTTGGCTCCCTTTTCC (SEQ NO: 78) | TCACCCACGTGTTACTCACC (SEQ NO: 79) | GCCCGCACGCTCACAGTTAAG (SEQ NO: 80) | GTCTGGGCCGTATCTCAGTC (SEQ NO: 81) | CGTCACCCCACCAACAAG (SEQ NO: 82) |
|---|---|---|---|---|---|---|---|
| Neisseria gonorrhoeae | TGTCGGTTTCTTTGAAGCAG (SEQ NO 83) | CCGGTACGTTCCGATATGTT (SEQ NO: 84) | GCAGACCAGAAGTTAAAAAGTTAGAGA (SEQ NO: 85) | ATCAGTTATCCCCCGCTACC (SEQ NO: 86) | GGGGATTTCACATCCTGCT (SEQ NO: 87) | ACTCGAGTCACCCAGTTCAG (SEQ NO: 88) | CTACTGATCGTCGCCTTGGT (SEQ NO: 89) |
| Porphyromonas gingivalis | GGGTAATAATGGCCTCTGA (SEQ NO 90) | CCCTCGACTTCCATGTGTTA (SEQ NO: 91) | CGAGGTGTACTACCCTGATAAATCG (SEQ NO: 92) | CCTATCGCTAGCGTTCATCC (SEQ NO: 93) | GTTTCAACGGCAGGCTGA (SEQ NO: 94) | GAGCGCTCAGGTTTCACC (SEQ NO: 95) | GTCCGTCTTTCAACGGGTTA (SEQ NO: 96) |
| Treponema pallidum | GATCCTGGCTCAGAACGAAC (SEQ NO 97) | GCAGATTACCCACGCGTTAC (SEQ NO: 98) | CCTGGAAACGGGGTTTAGA (SEQ NO: 99) | TTACTCACCAGTCCGCCACT (SEQ NO: 100) | GATTCCACCCCTACACTTGG (SEQ NO: 101) | GTTTCCCCTCCGTGATTCTA (SEQ NO: 102) | TCTCAGGTGGATACGCATC (SEQ NO: 103) |
| Vibrio cholerae | GCAATCATTCAGCACAGTCAA (SEQ NO 104) | TCGACTTGCATGTGTTAGGC (SEQ NO: 105) | CAGTATTCATTGAGCCGAAGC (SEQ NO: 106) | ATGGTTATCCCCCTCTACCG (SEQ NO: 107) | GTCAGTTTCAAATGCGATTCC (SEQ NO: 108) | TGCGATTCCTAGGTTCAGC (SEQ NO: 109) | CAGACCAGCTAGGGATCGTC (SEQ NO: 110) |

FIG. 7 cont.

SEQUENCE LISTING

<160> NUMBER OF SEQ ID NOS: 110

<210> SEQ ID NO 1
<211> LENGTH: 20
<212> TYPE: DNA
<213> ORGANISM: Mycobacterium avium

<400> SEQUENCE: 1
ttggccatac ctagcactcc          20

<210> SEQ ID NO 2
<211> LENGTH: 20
<212> TYPE: DNA
<213> ORGANISM: Mycobacterium avium

<400> SEQUENCE: 2
gattgcccac gtgttactca          20

<210> SEQ ID NO 3
<211> LENGTH: 21
<212> TYPE: DNA
<213> ORGANISM: Mycobacterium avium

<400> SEQUENCE: 3
gcccgcacgc tcacagttaa g          21

<210> SEQ ID NO 4
<211> LENGTH: 19
<212> TYPE: DNA
<213> ORGANISM: Aeromonas hydrophila

<400> SEQUENCE: 4
attgagccgc cttaacagg          19

<210> SEQ ID NO 5
<211> LENGTH: 19
<212> TYPE: DNA
<213> ORGANISM: Aeromonas hydrophila

<400> SEQUENCE: 5
aactgttatc cccctcgac          19

<210> SEQ ID NO 6
<211> LENGTH: 23
<212> TYPE: DNA
<213> ORGANISM: Aeromonas hydrophila

<400> SEQUENCE: 6
ctacaagact ctagctggac agt          23

<210> SEQ ID NO 7
<211> LENGTH: 22
<212> TYPE: DNA
<213> ORGANISM: Bacillus anthracis

<400> SEQUENCE: 7
acaaacaacg tgaaacgtca at          22

<210> SEQ ID NO 8
<211> LENGTH: 20
<212> TYPE: DNA
<213> ORGANISM: Bacillus anthracis

<400> SEQUENCE: 8
gtccgccgct aacttcataa          20

<210> SEQ ID NO 9
<211> LENGTH: 25
<212> TYPE: DNA
<213> ORGANISM: Bacillus anthracis

<400> SEQUENCE: 9
aactttattg gagagtttga tcctg                                      25

<210> SEQ ID NO 10
<211> LENGTH: 20
<212> TYPE: DNA
<213> ORGANISM: Bacillus anthracis

<400> SEQUENCE: 10
cccggagtta tcccagtctt                                            20

<210> SEQ ID NO 11
<211> LENGTH: 20
<212> TYPE: DNA
<213> ORGANISM: Bacillus anthracis

<400> SEQUENCE: 11
cagtttccaa tgaccctcca                                            20

<210> SEQ ID NO 12
<211> LENGTH: 21
<212> TYPE: DNA
<213> ORGANISM: Bacillus anthracis

<400> SEQUENCE: 12
tgcactcaag tctcccagtt t                                          21

<210> SEQ ID NO 13
<211> LENGTH: 20
<212> TYPE: DNA
<213> ORGANISM: Bacillus anthracis

<400> SEQUENCE: 13
gagccgttac ctcaccaact                                            20

<210> SEQ ID NO 14
<211> LENGTH: 20
<212> TYPE: DNA
<213> ORGANISM: Bordetella pertussis

<400> SEQUENCE: 14
gatcagggtc cacacacaga                                            20

<210> SEQ ID NO 15
<211> LENGTH: 20
<212> TYPE: DNA
<213> ORGANISM: Bordetella pertussis

<400> SEQUENCE: 15
ccacgctttc gcgtagttat                                            20

<210> SEQ ID NO 16
<211> LENGTH: 20
<212> TYPE: DNA
<213> ORGANISM: Bordetella pertussis

<400> SEQUENCE: 16
aagcgatacg gatcctggtt                                            20

<210> SEQ ID NO 17
<211> LENGTH: 20
<212> TYPE: DNA
<213> ORGANISM: Bordetella pertussis -continued

```
<400> SEQUENCE: 17
ccgacttgca tgtgtaaagc                                               20

<210> SEQ ID NO 18
<211> LENGTH: 21
<212> TYPE: DNA
<213> ORGANISM: Bordetella pertussis

<400> SEQUENCE: 18
gcccggtagt taaaaatgca g                                             21

<210> SEQ ID NO 19
<211> LENGTH: 21
<212> TYPE: DNA
<213> ORGANISM: Bordetella pertussis

<400> SEQUENCE: 19
aaggttaagc cctgggattt c                                             21

<210> SEQ ID NO 20
<211> LENGTH: 20
<212> TYPE: DNA
<213> ORGANISM: Bordetella pertussis

<400> SEQUENCE: 20
tcctctcaaa ccagctacgg                                               20

<210> SEQ ID NO 21
<211> LENGTH: 23
<212> TYPE: DNA
<213> ORGANISM: Borrelia burgdorferi

<400> SEQUENCE: 21
gccaaaagaa taaacaaaac ctg                                           23

<210> SEQ ID NO 22
<211> LENGTH: 20
<212> TYPE: DNA
<213> ORGANISM: Borrelia burgdorferi

<400> SEQUENCE: 22
ccgtttgact tgcatgctta                                               20

<210> SEQ ID NO 23
<211> LENGTH: 22
<212> TYPE: DNA
<213> ORGANISM: Borrelia burgdorferi

<400> SEQUENCE: 23
ttggaagatg agagaaggga ag                                            22

<210> SEQ ID NO 24
<211> LENGTH: 20
<212> TYPE: DNA
<213> ORGANISM: Borrelia burgdorferi

<400> SEQUENCE: 24
ttcgccactg aatgtattgc                                               20

<210> SEQ ID NO 25
<211> LENGTH: 21
<212> TYPE: DNA
```

<213> ORGANISM: Borrelia burgdorferi

<400> SEQUENCE: 25
agtttccaac ataggtccac a    21

<210> SEQ ID NO 26
<211> LENGTH: 23
<212> TYPE: DNA
<213> ORGANISM: Borrelia burgdorferi

<400> SEQUENCE: 26
agttgagctg tggtatttta tgc    23

<210> SEQ ID NO 27
<211> LENGTH: 20
<212> TYPE: DNA
<213> ORGANISM: Borrelia burgdorferi

<400> SEQUENCE: 27
tgccttggta ggcatttacc    20

<210> SEQ ID NO 28
<211> LENGTH: 27
<212> TYPE: DNA
<213> ORGANISM: Campylobacter jejuni

<400> SEQUENCE: 28
tttaggcata agcaattatg taaaatc    27

<210> SEQ ID NO 29
<211> LENGTH: 20
<212> TYPE: DNA
<213> ORGANISM: Campylobacter jejuni

<400> SEQUENCE: 29
cgttcactct gagccaggat    20

<210> SEQ ID NO 30
<211> LENGTH: 26
<212> TYPE: DNA
<213> ORGANISM: Campylobacter jejuni

<400> SEQUENCE: 30
gatttaggca taagcaatta tgtaaa    26

<210> SEQ ID NO 31
<211> LENGTH: 20
<212> TYPE: DNA
<213> ORGANISM: Campylobacter jejuni

<400> SEQUENCE: 31
agccaggatc aaactctcca    20

<210> SEQ ID NO 32
<211> LENGTH: 22
<212> TYPE: DNA
<213> ORGANISM: Campylobacter jejuni

<400> SEQUENCE: 32
gagacttgat aatccgccta cg    22

<210> SEQ ID NO 33
<211> LENGTH: 17

<212> TYPE: DNA
<213> ORGANISM: Campylobacter jejuni

<400> SEQUENCE: 33
cctacgcgcc ctttacg                17

<210> SEQ ID NO 34
<211> LENGTH: 20
<212> TYPE: DNA
<213> ORGANISM: Campylobacter jejuni

<400> SEQUENCE: 34
tcgtttccaa ctgttgtcct             20

<210> SEQ ID NO 35
<211> LENGTH: 23
<212> TYPE: DNA
<213> ORGANISM: Clostridium difficile

<400> SEQUENCE: 35
aagaaacaaa ccataaagcc aga          23

<210> SEQ ID NO 36
<211> LENGTH: 20
<212> TYPE: DNA
<213> ORGANISM: Clostridium difficile

<400> SEQUENCE: 36
tcgctcaact tgcatgtgtt             20

<210> SEQ ID NO 37
<211> LENGTH: 27
<212> TYPE: DNA
<213> ORGANISM: Clostridium difficile

<400> SEQUENCE: 37
tttgataaca atagtatctg agcctga      27

<210> SEQ ID NO 38
<211> LENGTH: 20
<212> TYPE: DNA
<213> ORGANISM: Clostridium difficile

<400> SEQUENCE: 38
ggtaggttac ccacgcgtta             20

<210> SEQ ID NO 39
<211> LENGTH: 20
<212> TYPE: DNA
<213> ORGANISM: Clostridium difficile

<400> SEQUENCE: 39
tccactctcc tctcctgcac             20

<210> SEQ ID NO 40
<211> LENGTH: 21
<212> TYPE: DNA
<213> ORGANISM: Clostridium difficile

<400> SEQUENCE: 40
tgcactcaag tctcccagtt t           21

<210> SEQ ID NO 41

```
<211> LENGTH: 20
<212> TYPE: DNA
<213> ORGANISM: Clostridium difficile

<400> SEQUENCE: 41
cgtaggagtt tggaccgtgt                                                  20

<210> SEQ ID NO 42
<211> LENGTH: 20
<212> TYPE: DNA
<213> ORGANISM: Escherichia coli

<400> SEQUENCE: 42
gtcgcaagac gaaaaatgaa                                                  20

<210> SEQ ID NO 43
<211> LENGTH: 20
<212> TYPE: DNA
<213> ORGANISM: Escherichia coli

<400> SEQUENCE: 43
tcgacttgca tgtgttaggc                                                  20

<210> SEQ ID NO 44
<211> LENGTH: 26
<212> TYPE: DNA
<213> ORGANISM: Escherichia coli

<400> SEQUENCE: 44
tctttgagca tcaaactttt aaattg                                           26

<210> SEQ ID NO 45
<211> LENGTH: 20
<212> TYPE: DNA
<213> ORGANISM: Escherichia coli

<400> SEQUENCE: 45
caggcagttt cccagacatt                                                  20

<210> SEQ ID NO 46
<211> LENGTH: 20
<212> TYPE: DNA
<213> ORGANISM: Escherichia coli

<400> SEQUENCE: 46
tcagatgcag ttcccaggtt                                                  20

<210> SEQ ID NO 47
<211> LENGTH: 18
<212> TYPE: DNA
<213> ORGANISM: Escherichia coli

<400> SEQUENCE: 47
cccggggatt tcacatct                                                    18

<210> SEQ ID NO 48
<211> LENGTH: 20
<212> TYPE: DNA
<213> ORGANISM: Escherichia coli

<400> SEQUENCE: 48
ctcagaccag ctagggatcg                                                  20
```

```
<210> SEQ ID NO 49
<211> LENGTH: 25
<212> TYPE: DNA
<213> ORGANISM: Haemophilus influenzae

<400> SEQUENCE: 49
cgattgaact tgaattgaag agttt                                  25

<210> SEQ ID NO 50
<211> LENGTH: 20
<212> TYPE: DNA
<213> ORGANISM: Haemophilus influenzae

<400> SEQUENCE: 50
cactcgtcag caagaaagca                                        20

<210> SEQ ID NO 51
<211> LENGTH: 27
<212> TYPE: DNA
<213> ORGANISM: Haemophilus influenzae

<400> SEQUENCE: 51
ttgaagtctt aataggtgct taactga                                27

<210> SEQ ID NO 52
<211> LENGTH: 20
<212> TYPE: DNA
<213> ORGANISM: Haemophilus influenzae

<400> SEQUENCE: 52
ctttctcctg ctaccgttcg                                        20

<210> SEQ ID NO 53
<211> LENGTH: 20
<212> TYPE: DNA
<213> ORGANISM: Haemophilus influenzae

<400> SEQUENCE: 53
ctgaaatgca attcccaggt                                        20

<210> SEQ ID NO 54
<211> LENGTH: 19
<212> TYPE: DNA
<213> ORGANISM: Haemophilus influenzae

<400> SEQUENCE: 54
ggggctttca cacctcact                                         19

<210> SEQ ID NO 55
<211> LENGTH: 20
<212> TYPE: DNA
<213> ORGANISM: Haemophilus influenzae

<400> SEQUENCE: 55
cagtcccgca ctttcatctt                                        20

<210> SEQ ID NO 56
<211> LENGTH: 18
<212> TYPE: DNA
<213> ORGANISM: Helicobacter pylori

<400> SEQUENCE: 56
gttgttagga ataacaac                                          18
```

```
<210> SEQ ID NO 57
<211> LENGTH: 20
<212> TYPE: DNA
<213> ORGANISM: Helicobacter pylori

<400> SEQUENCE: 57
agcttcatcg ttcgacttgc                                                    20

<210> SEQ ID NO 58
<211> LENGTH: 22
<212> TYPE: DNA
<213> ORGANISM: Helicobacter pylori

<400> SEQUENCE: 58
cgagttcttg tgatacgcta aa                                                 22

<210> SEQ ID NO 59
<211> LENGTH: 20
<212> TYPE: DNA
<213> ORGANISM: Helicobacter pylori

<400> SEQUENCE: 59
ttccaatggc tatcccaaac                                                    20

<210> SEQ ID NO 60
<211> LENGTH: 23
<212> TYPE: DNA
<213> ORGANISM: Helicobacter pylori

<400> SEQUENCE: 60
ctcccacact ctagaatagt agt                                                23

<210> SEQ ID NO 61
<211> LENGTH: 26
<212> TYPE: DNA
<213> ORGANISM: Helicobacter pylori

<400> SEQUENCE: 61
acactctaga atagtagttt caaatg                                             26

<210> SEQ ID NO 62
<211> LENGTH: 20
<212> TYPE: DNA
<213> ORGANISM: Legionella pneumophila

<400> SEQUENCE: 62
agagctagtg ccggaattga                                                    20

<210> SEQ ID NO 63
<211> LENGTH: 20
<212> TYPE: DNA
<213> ORGANISM: Legionella pneumophila

<400> SEQUENCE: 63
tgagtttccc caagttgtcc                                                    20

<210> SEQ ID NO 64
<211> LENGTH: 21
<212> TYPE: DNA
<213> ORGANISM: Legionella pneumophila

<400> SEQUENCE: 64
gacaaactgt gtgggcactt t                                                  21
```

<210> SEQ ID NO 65
<211> LENGTH: 20
<212> TYPE: DNA
<213> ORGANISM: Legionella pneumophila

<400> SEQUENCE: 65
gctagacaat gctgccgttc 20

<210> SEQ ID NO 66
<211> LENGTH: 21
<212> TYPE: DNA
<213> ORGANISM: Legionella pneumophila

<400> SEQUENCE: 66
aggttaagcc caggaatttc a 21

<210> SEQ ID NO 67
<211> LENGTH: 21
<212> TYPE: DNA
<213> ORGANISM: Legionella pneumophila

<400> SEQUENCE: 67
attatctgac cgtcccaggt t 21

<210> SEQ ID NO 68
<211> LENGTH: 18
<212> TYPE: DNA
<213> ORGANISM: Legionella pneumophila

<400> SEQUENCE: 68
gtccccagct ttcgtcct 18

<210> SEQ ID NO 69
<211> LENGTH: 24
<212> TYPE: DNA
<213> ORGANISM: Listeria monocytogenes

<400> SEQUENCE: 69
agctgttttc aacaaaacaa acta 24

<210> SEQ ID NO 70
<211> LENGTH: 20
<212> TYPE: DNA
<213> ORGANISM: Listeria monocytogenes

<400> SEQUENCE: 70
cctgagccag gatcaaactc 20

<210> SEQ ID NO 71
<211> LENGTH: 27
<212> TYPE: DNA
<213> ORGANISM: Listeria monocytogenes

<400> SEQUENCE: 71
gctgttttca acaaaacaaa ctagtaa 27

<210> SEQ ID NO 72
<211> LENGTH: 20
<212> TYPE: DNA
<213> ORGANISM: Listeria monocytogenes

<400> SEQUENCE: 72
agcaagctct tcctccgttc                                               20

<210> SEQ ID NO 73
<211> LENGTH: 20
<212> TYPE: DNA
<213> ORGANISM: Listeria monocytogenes

<400> SEQUENCE: 73
ggggctttca catcagactt                                               20

<210> SEQ ID NO 74
<211> LENGTH: 18
<212> TYPE: DNA
<213> ORGANISM: Listeria monocytogenes

<400> SEQUENCE: 74
aatgaccctc cccggtta                                                 18

<210> SEQ ID NO 75
<211> LENGTH: 20
<212> TYPE: DNA
<213> ORGANISM: Listeria monocytogenes

<400> SEQUENCE: 75
aggttgccca cgtgttactc                                               20

<210> SEQ ID NO 76
<211> LENGTH: 20
<212> TYPE: DNA
<213> ORGANISM: Mycobacterium tuberculosis

<400> SEQUENCE: 76
tttccaaagg gagtgtttgg                                               20

<210> SEQ ID NO 77
<211> LENGTH: 20
<212> TYPE: DNA
<213> ORGANISM: Mycobacterium tuberculosis

<400> SEQUENCE: 77
acccagtttc ccaggcttat                                               20

<210> SEQ ID NO 78
<211> LENGTH: 20
<212> TYPE: DNA
<213> ORGANISM: Mycobacterium tuberculosis

<400> SEQUENCE: 78
tacctttggc tcccttttcc                                               20

<210> SEQ ID NO 79
<211> LENGTH: 20
<212> TYPE: DNA
<213> ORGANISM: Mycobacterium tuberculosis

<400> SEQUENCE: 79
tcacccacgt gttactcacc                                               20

<210> SEQ ID NO 80
<211> LENGTH: 21
<212> TYPE: DNA
<213> ORGANISM: Mycobacterium tuberculosis

<400> SEQUENCE: 80
gcccgcacgc tcacagttaa g                                              21

<210> SEQ ID NO 81
<211> LENGTH: 20
<212> TYPE: DNA
<213> ORGANISM: Mycobacterium tuberculosis

<400> SEQUENCE: 81
gtctgggccg tatctcagtc                                                20

<210> SEQ ID NO 82
<211> LENGTH: 18
<212> TYPE: DNA
<213> ORGANISM: Mycobacterium tuberculosis

<400> SEQUENCE: 82
cgtcacccca ccaacaag                                                  18

<210> SEQ ID NO 83
<211> LENGTH: 20
<212> TYPE: DNA
<213> ORGANISM: Neisseria gonorrhoeae

<400> SEQUENCE: 83
tgtcggtttc tttgaagcag                                                20

<210> SEQ ID NO 84
<211> LENGTH: 20
<212> TYPE: DNA
<213> ORGANISM: Neisseria gonorrhoeae

<400> SEQUENCE: 84
ccggtacgtt ccgatatgtt                                                20

<210> SEQ ID NO 85
<211> LENGTH: 27
<212> TYPE: DNA
<213> ORGANISM: Neisseria gonorrhoeae

<400> SEQUENCE: 85
gcagaccaga agttaaaaag ttagaga                                        27

<210> SEQ ID NO 86
<211> LENGTH: 20
<212> TYPE: DNA
<213> ORGANISM: Neisseria gonorrhoeae

<400> SEQUENCE: 86
atcagttatc ccccgctacc                                                20

<210> SEQ ID NO 87
<211> LENGTH: 19
<212> TYPE: DNA
<213> ORGANISM: Neisseria gonorrhoeae

<400> SEQUENCE: 87
ggggatttca catcctgct                                                 19

<210> SEQ ID NO 88
<211> LENGTH: 20
<212> TYPE: DNA
<213> ORGANISM: Neisseria gonorrhoeae

```
<400> SEQUENCE: 88
actcgagtca cccagttcag                                              20

<210> SEQ ID NO 89
<211> LENGTH: 20
<212> TYPE: DNA
<213> ORGANISM: Neisseria gonorrhoeae

<400> SEQUENCE: 89
ctactgatcg tcgccttggt                                              20

<210> SEQ ID NO 90
<211> LENGTH: 20
<212> TYPE: DNA
<213> ORGANISM: Porphyromonas gingivalis

<400> SEQUENCE: 90
gggtaataat cggcgtctga                                              20

<210> SEQ ID NO 91
<211> LENGTH: 20
<212> TYPE: DNA
<213> ORGANISM: Porphyromonas gingivalis

<400> SEQUENCE: 91
ccctcgactt gcatgtgtta                                              20

<210> SEQ ID NO 92
<211> LENGTH: 24
<212> TYPE: DNA
<213> ORGANISM: Porphyromonas gingivalis

<400> SEQUENCE: 92
cgaggtgtac tacctgataa atcg                                         24

<210> SEQ ID NO 93
<211> LENGTH: 20
<212> TYPE: DNA
<213> ORGANISM: Porphyromonas gingivalis

<400> SEQUENCE: 93
cctatcgcta gcgttcatcc                                              20

<210> SEQ ID NO 94
<211> LENGTH: 18
<212> TYPE: DNA
<213> ORGANISM: Porphyromonas gingivalis

<400> SEQUENCE: 94
gtttcaacgg caggctga                                                18

<210> SEQ ID NO 95
<211> LENGTH: 18
<212> TYPE: DNA
<213> ORGANISM: Porphyromonas gingivalis

<400> SEQUENCE: 95
gagcgctcag gtttcacc                                                18

<210> SEQ ID NO 96
<211> LENGTH: 20
<212> TYPE: DNA
<213> ORGANISM: Porphyromonas gingivalis
```

```
<400> SEQUENCE: 96
gtccgtcttt caacgggtta                                          20

<210> SEQ ID NO 97
<211> LENGTH: 20
<212> TYPE: DNA
<213> ORGANISM: Treponema pallidum

<400> SEQUENCE: 97
gatcctggct cagaacgaac                                          20

<210> SEQ ID NO 98
<211> LENGTH: 20
<212> TYPE: DNA
<213> ORGANISM: Treponema pallidum

<400> SEQUENCE: 98
gcagattacc cacgcgttac                                          20

<210> SEQ ID NO 99
<211> LENGTH: 19
<212> TYPE: DNA
<213> ORGANISM: Treponema pallidum

<400> SEQUENCE: 99
cctggaaacg gggtttaga                                           19

<210> SEQ ID NO 100
<211> LENGTH: 20
<212> TYPE: DNA
<213> ORGANISM: Treponema pallidum

<400> SEQUENCE: 100
ttactcacca gtccgccact                                          20

<210> SEQ ID NO 101
<211> LENGTH: 20
<212> TYPE: DNA
<213> ORGANISM: Treponema pallidum

<400> SEQUENCE: 101
gattccaccc ctacacttgg                                          20

<210> SEQ ID NO 102
<211> LENGTH: 20
<212> TYPE: DNA
<213> ORGANISM: Treponema pallidum

<400> SEQUENCE: 102
gtttcccctc cgtgattcta                                          20

<210> SEQ ID NO 103
<211> LENGTH: 20
<212> TYPE: DNA
<213> ORGANISM: Treponema pallidum

<400> SEQUENCE: 103
tctcaggtcg gatacccatc                                          20

<210> SEQ ID NO 104
<211> LENGTH: 21
<212> TYPE: DNA
```

```
<213> ORGANISM: Vibrio cholerae

<400> SEQUENCE: 104
gcaatcattc agcacagtca a                                              21

<210> SEQ ID NO 105
<211> LENGTH: 20
<212> TYPE: DNA
<213> ORGANISM: Vibrio cholerae

<400> SEQUENCE: 105
tcgacttgca tgtgttaggc                                                20

<210> SEQ ID NO 106
<211> LENGTH: 21
<212> TYPE: DNA
<213> ORGANISM: Vibrio cholerae

<400> SEQUENCE: 106
cagtattcat tgagccgaag c                                              21

<210> SEQ ID NO 107
<211> LENGTH: 20
<212> TYPE: DNA
<213> ORGANISM: Vibrio cholerae

<400> SEQUENCE: 107
atggttatcc ccctctaccg                                                20

<210> SEQ ID NO 108
<211> LENGTH: 21
<212> TYPE: DNA
<213> ORGANISM: Vibrio cholerae

<400> SEQUENCE: 108
gtcagtttca aatgcgattc c                                              21

<210> SEQ ID NO 109
<211> LENGTH: 19
<212> TYPE: DNA
<213> ORGANISM: Vibrio cholerae

<400> SEQUENCE: 109
tgcgattcct aggttgagc                                                 19

<210> SEQ ID NO 110
<211> LENGTH: 20
<212> TYPE: DNA
<213> ORGANISM: Vibrio cholerae

<400> SEQUENCE: 110
cagaccagct agggatcgtc                                                20
```

RATIOMETRIC PRE-RRNA ANALYSIS

FEDERALLY SPONSORED RESEARCH OR DEVELOPMENT

The compositions and methods disclosed herein were developed under STAR Research Assistance Agreements #FP91698201-0 and #R833011 awarded by the Environmental Protection Agency. As such, the government may have certain rights in the invention.

TECHNICAL FIELD

The invention relates to detecting and determining the presence of viable cells in a sample. More specifically, the invention relates to detecting viable cells present in very small numbers in a sample. Included are compositions and methods for detecting ribosomal RNA precursors (pre-rRNA) as dynamic indicators of viable microorganisms in a sample.

BACKGROUND

Microorganisms such as bacterial pathogens can be difficult to cultivate from complex clinical and environmental samples. They may be present in small numbers or in injured and aged physiological states with poor plating efficiency. Samples often have competing microbial flora that overgrow pathogens on non-selective media, while selective media can reduce yield and select against some strains. Most culture-based detection methods require 1-3 days to yield results, too slow for many circumstances, especially life-threatening ones.

An alternative to bacteriological culture is nucleic acid amplification testing (NAAT). The most common type of NAAT, the polymerase chain reaction (PCR), is rapid and sensitive. A limitation of PCR is its inability to distinguish viable pathogen cells from non-viable cells, from free nucleic acids in samples, and from contaminating nucleic acids introduced during the testing process. PCR is also mechanistically complex and susceptible to inhibition by substances in samples. These limitations are especially problematic when PCR is used to assess the efficacy of antimicrobial treatment, disinfection (e.g. water treatment), and clean-up processes.

In order to improve the sensitivity and specificity of NAAT for viable microorganisms it would be valuable to reduce or eliminate the false-positive detection of non-viable microorganisms and free DNA. One approach is the detection of microbial RNA rather than DNA. RNA is considered less stable than DNA in solution and in dead cells. Species-specific probes for ribosomal RNA (rRNA) or messenger RNA (mRNA) are known. However, microbial mRNA is difficult to detect due to its instability and low abundance (Gedalanga and Olson. 2009. Development of a quantitative PCR method to differentiate between viable and nonviable bacteria in environmental water samples. *Appl Microbiol Biotechnol.* 82:587-596). Conversely, mature rRNA is fairly stable and can persist within dead bacterial cells for long periods of time.

SUMMARY

To improve sensitivity and specificity for viable cells, assays for microbial rRNA precursors (pre-rRNA) may be used. Pre-rRNAs are intermediates in rRNA synthesis generated by rapid nucleolytic cleavage of the polycistronic rrs-rrl-rrf operon transcript. Leader and tail fragments are subsequently removed in slower reactions tied to ribosome assembly, yielding the mature rRNA subunits. In growing bacterial cells, pre-rRNAs account for a large fraction of total rRNA. Pre-rRNAs are significantly more abundant and easier to detect than even the most strongly-expressed mRNA molecules in bacteria. Moreover, their intracellular copy numbers rapidly increase upon nutritional stimulation, a dynamic property that facilitates the interpretation of borderline results, thereby improving the functional sensitivity of tests for cells present in very small numbers in samples. Additionally, they frequently have species-specific sequences that facilitate their detection in complex samples by NAAT.

As disclosed herein, NAATs have been developed that detect species-specific pre-rRNA molecules. Pre-rRNAs are intermediates in the synthesis of mature rRNA. They are abundant cellular components with highly species-specific nucleotide sequences. This makes them good targets for detecting microbial pathogens in complex samples. Pre-rRNA copy number increases by orders of magnitude when microbial cells undergo nutritional stimulation. This response is very rapid (<1 generation time) and easy to detect due to pre-rRNA abundance in stimulated cells. Quantitative PCR measurement of pre-rRNA in stimulated and control samples yields numerical ratios. If positive, these ratios confirm the presence of intact, viable pathogen cells in samples. When quantitative PCR signals are very weak, positive ratios increase confidence that assay results represent true positive results. This improves the functional sensitivity of assays.

Additional aspects and advantages will be apparent from the following detailed description of preferred embodiments, which proceeds with reference to the accompanying drawings.

BRIEF DESCRIPTION OF THE DRAWINGS

FIG. 6 lists example genera and species of target microorganisms that may be targeted by the methods of RPA disclosed herein.

FIG. 7 shows examples of qPCR primers, including alternative forward, reverse, and reverse transcriptase primers for the referenced organisms.

DETAILED DESCRIPTION OF PREFERRED EMBODIMENTS

Figure 1:
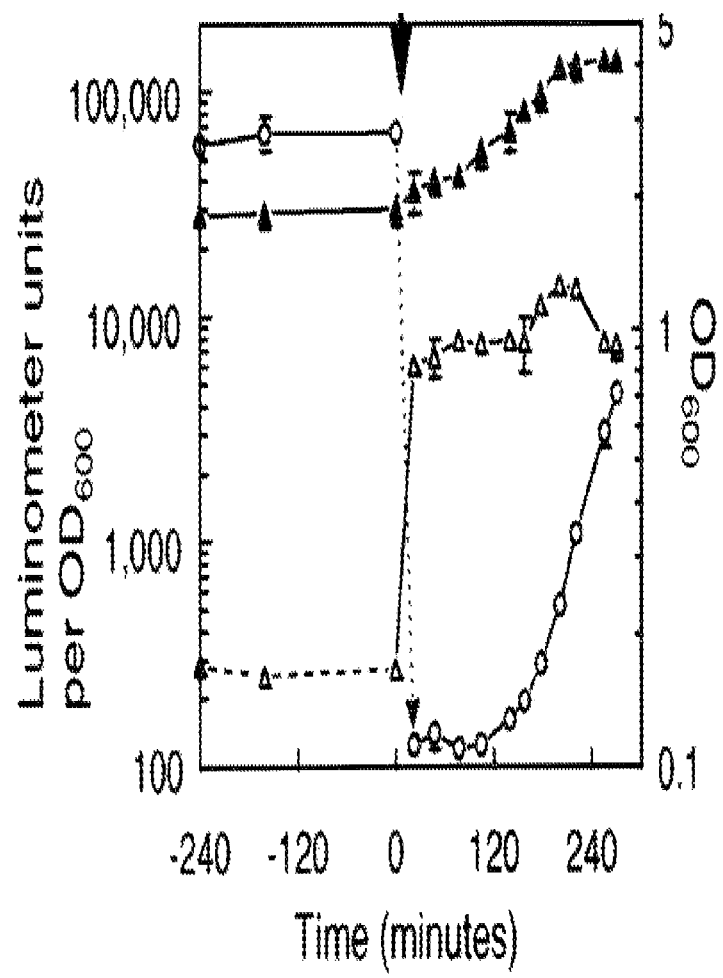
FIG. 1 shows pre-16S rRNA and mature 16S rRNA pools during outgrowth from stationary phase on LB broth.

Disclosed are materials, compositions, and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed that, while specific reference of each various individual and collective combinations and permutation of these compounds may not be explicitly disclosed, each is specifically contemplated and described herein. For example, if an oligonucleotide is disclosed and discussed and a number of modifications that can be made to a number of molecules including the oligonucleotide are discussed, each and every combination and permutation of oligonucleotide and the modifications that are possible are specifically contemplated, unless specifically indicated to the contrary. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, equivalents to the specific embodiments of the method and compositions described herein. Such equivalents are intended to be encompassed by the included claims.

It is also to be understood that the terminology used herein is for the purpose of describing particular embodiments only, and is not intended to limit the scope of the present invention which will be limited only by the appended claims.

Unless defined otherwise, all technical and scientific terms used herein have the meanings that would be commonly understood by one of skill in the art in the context of the present specification.

It must be noted that as used herein and in the appended claims, the singular forms "a," "an," and "the" include plural reference unless the context clearly dictates otherwise. Thus, for example, reference to "a microorganism" includes a plurality of such microorganisms, reference to "the microorganism" is a reference to one or more microorganisms and equivalents thereof known to those skilled in the art, and so forth.

Compounds and methods are described herein that exploit pre-rRNA replenishment as the basis for NAATs specific to viable microbial cells. When microorganism growth slows or stops, pre-rRNA synthesis decreases but its processing continues, resulting in active and substantial drainage of pre-rRNA pools. Pre-rRNA pools are rapidly replenished when growth-limited cells are given fresh nutrients. Such fluctuations occur consistently in intact, viable microbial cells. They are not seen in dead cells, with free nucleic acids, or with other types of background assay "noise".

Pre-rRNA sequences have specificity comparable to the most hypervariable regions of mature rRNA. Therefore, viable microbial cells of a given species can be distinguished from other species by pre-rRNA detection. Moreover, viable microbial cells can be distinguished from dead cells of the same species by measuring their pre-rRNA in samples that have been briefly stimulated with nutrients. The level of pre-rRNA present in the stimulated sample is compared to a non-stimulated control sample, and when species-specific pre-rRNA in the stimulated sample exceeds that of the control sample, the presence of viable cells is indicated. This ratiometric approach is referred to herein as Ratiometric Pre-rRNA Analysis (RPA).

As disclosed herein, RPA may be conducted by dividing a sample into two or more aliquots wherein at least one aliquot is nutritionally stimulated and at least one aliquot is treated as a non-stimulated control. The pre-rRNA levels in the nutritionally stimulated sample are compared with the pre-rRNA levels in the control sample wherein, the replenishment of pre-rRNA in the stimulated sample is indicative of viable cells in the sample.

In one embodiment, RPA may include the use of two equal aliquots of a sample, wherein one aliquot is nutritionally stimulated while the other is held in a non-nutritionally stimulated control. After nutritional stimulation for <1 generation time, species-specific pre-rRNA is quantified ratiometrically to determine the pre-rRNA stimulation ratio values. In one embodiment, nutritional stimulation may last for a period of <1 generation, <½ generation, <⅓ generation, <¼ generation, and <⅛ generation time of a target microorganism. The nutritional stimulation step is not of sufficient duration for even modest amplification of microbial numbers. As such, RPA is not a culture enrichment. In one such embodiment, pre-rRNA stimulation ratio values are the ratios of pre-rRNA levels in stimulated samples relative to control samples. In particular embodiments, pre-rRNA stimulation values are used to determine the presence of viable microbial of cells in a sample. For example, the presence of viable microorganisms is indicated when the pre-rRNA values in a nutritionally stimulated aliquot are greater than the pre-rRNA values in a non-stimulated control aliquot.

It has been found that, in specific embodiments, the methods of RPA disclosed herein may be used to detect viable target microorganisms that are substantially outnumbered by inactivated or dead microorganisms of the same species. In one embodiment, RPA may be conducted to detect viable microorganisms in a sample wherein approximately 0.01% to 99% of the target microorganisms are viable microorganisms. In one such embodiment, RPA may be used to detect the presence of viable target microorganisms that are present in a sample at a level of approximately 0.01%, 0.02%, 0.03%, 0.04%, 0.05%, 0.1%, 0.5%, 1.0%, 2.0%, 3.0% 4.0%, 5.0%, 10%, 15, 20%, 25%, 30%, 35%, 40%, 45%, 50%, 55%, 60%, 65%, 70%, 75%, 80%, 85%, 90%, and 95% of the total population of target microorganisms (live+dead). As used herein, the percentage of viable target microorganisms in a sample is the number of viable target microorganisms relative to the total number of target microorganisms, both viable and inactivated.

RPA as described herein can be conducted on various different types of specific samples. In one such embodiment, the sample as used herein can be a sample collected from any desired source or location that may potentially comprise cells of interest. In one embodiment, the sample may be taken from a liquid, a solid, a gas, a composite, a tissue, or any other desired substrate. The sample may be taken from an outdoor environment or an indoor environment, or in other embodiments, the sample may be a tissue, fluid, or swab sample taken from a subject. In one such embodiment, a tissue sample may be a blood, saliva, sputum, stool, urine, hair, skin, or any other sample taken from the body of a subject. For purposes of the present description, the term "subject" refers to a human, animal, or plant subject. Even further, a sample for analysis using the RPA methods described herein may be collected from a natural environment, industrial environment, health care environment, residential environment, agricultural environment, water distribution environment, wastewater treatment environment, food production or distribution environment, recreational environment, or any desired environment or combinations thereof. A sample may comprise inorganic and/or organic materials, and may be collected from a marine environment or fresh water environment, and may comprise dirt, rocks, soil, vegetation, air, and combinations thereof.

A sample suitable for RPA as described herein may include a cell of interest, which can be a prokaryotic cell or a eukaryotic cell. In particular embodiments, the microorganism may be a gram negative bacterium, a gram positive bacterium, or another type of bacterium. Therefore, the methods for RPA described herein may be applied for the detection of one or more microorganisms that have significance in one or more contexts including human and veterinary clinical settings. For instance, in one embodiment the methods of RPA as described herein may be used for the detection of foodborne and waterborne microorganisms. In another embodiment, RPA as disclosed herein may be used for biodefense and the detection of microorganisms used for bioweapons. In another embodiment, the methods of RPA as described herein may be used for infectious disease diagnosis or treatment monitoring. In another embodiment, the methods of RPA as described herein may be used for quality assurance of manufacturing processes including but not limited to food, drinks, or medical devices. In another embodiment, the methods of RPA as described herein may be used for assuring the effective sterilization, or maintenance of sterility, of devices and materials used in health care.

As shown in FIG. 6, RPA may be conducted with samples containing one or more microorganisms of interest including many species of microorganisms from many different genera. The methods of RPA disclosed herein are suited to the detection of species-specific pre-rRNAs, and in specific embodiments, RPA as disclosed herein may detect species-specific pre-rRNAs of microorganisms from one or more genera selected from *Acinetobacter, Actinobacillus, Aeromonas, Arcobacter, Bacteroides, Bordetella, Borrelia, Brucella, Burkholderia, Campylobacter, Citrobacter, Cronobacter, Edwardsiella, Enterobacter, Escherichia, Eubacterium, Francisella, Fusobacterium, Haemophilus, Helicobacter, Klebsiella, Legionella, Leptospira, Moraxella, Morganella, Neisseria, Pasteurella, Plesiomonas, Porphyromonas, Prevotella, Proteus, Providencia, Pseudomonas, Salmonella, Serratia, Shigella, Stenotrophomonas, Treponema, Veillonella, Vibrio, Yersinia, Actinomyces, Bacillus, Bifidobacterium, Clostridium, Corynebacterium, Enterococcus, Lactobacillus, Listeria, Micrococcus, Mobiluncus, Mycobacterium, Nocardia, Peptostreptococcus, Propionibacterium, Rhodococcus, Staphylococcus, Streptococcus*, and *Streptomyces*.

The methods for RPA comprise dividing a sample into two or more aliquots wherein at least one aliquot is nutritionally stimulated and at least one aliquot is treated as a non-stimulated control. In one embodiment, the material present in the nutritionally stimulated aliquot is pelleted, washed, and placed under desired microbial culture conditions. Microbial culture conditions as disclosed herein are the environmental and nutrient conditions generally known by those of skill in the art appropriate for a desired growth of a target organism. Generally, optimized microbial culture conditions may include nutrient media, temperature, humidity, oxygen tension, the presence of specific micro- or macro-nutrients, absence of inhibitors, and pressure, appropriate for a target microorganism. In one such embodiment, the nutritionally stimulated aliquot is incubated or cultured for a desired period of time under conditions wherein the aliquot is supplemented with culture media appropriate for a target microorganism. For example, where the target organism is a gram negative bacillus *Aeromonas hydrophila* the sample may be incubated with a culture media comprising a nutrient broth culture media. In another example, the target organism is *Mycobacterium avium* and the microbial culture conditions may include incubating the sample with Middlebrook 7H9 medium. In another example, the target organism is an anaerobe and the nutritional stimulation conditions may include low oxygen tension. In another example, the target organism is a pathogen such as *Listeria* that lives in an intracellular environment with limited iron availability, and the nutritional stimulation conditions may include the provision of iron. In one embodiment, the non-nutritionally stimulated control aliquot is incubated under control conditions designed to maintain the status of a target microorganism. In one such embodiment, the control aliquot is incubated in water or buffer. In another embodiment, the control aliquot is maintained in an unfavorable atmosphere, such as atmospheric oxygen concentration in the case of anaerobe detection.

The methods of RPA described herein typically include the quantification of one or more pre-rRNA molecules that have been isolated from target microorganisms in a sample. In one such embodiment, pre-rRNA are isolated from a sample according to nucleic acid extraction techniques know by those of skill in the art. For example, the cells in the sample may be lysed and the nucleic acids extracted according to standard methods such as a phenol-chloroform extraction method. Exemplary methods of nucleic acid extraction, including pre-rRNA extraction and quantification, are disclosed in U.S. Pat. No. 5,712,095, Cangelosi et al. 1997, and Cangelosi et al. 1996 (Cangelosi, G. A. and W. H. Brabant. 1997. Depletion of pre-16S rRNA in starved *Escherichia coli* cells. *J. Bacteriol.* 179:4457-4463; Cangelosi, G. A., W. H. Brabant, T. B. Britschgi, and C. K. Wallis. 1996. Detection of rifampin- and ciprofloxacin-resistant *Mycobacterium tuberculosis* by using species-specific assays for precursor rRNA. *Antimicrob. Agents Chemother.* 40:1790-1795) each of which are incorporated herein by reference.

The quantification of pre-rRNA molecules includes the use of nucleic acid amplification technologies. In one such embodiment, the nucleic acid amplification technology may be a PCR-based technology. In another such embodiment, nucleic acids may be amplified by a non-PCR based method such as an isothermal amplification method such as, for example, Nucleic Acid Sequence Based Amplification (NASBA). Examples of methods of nucleic acid amplification are disclosed by Gill and Ghaemi, 2008 (Pooria Gill and Amir Ghaemi. 2008. Nucleic acid isothermal amplification technologies—a review. *Nucleosides, Nucleotides, and Nucleic Acids.* 27:224-243), incorporated by reference herein. In one embodiment of RPA described herein, RT-qPCR may be used to quantify species-specific pre-rRNA from a sample to determine the pre-rRNA stimulation values. RT-qPCR uses reverse transcriptase to convert RNA to cDNA, which is then measured by standard quantitative PCR (qPCR).

The methods of RPA disclosed herein may use oligonucleotide primers designed to target pre-rRNA sequences of a target microorganism, and primers for use with RPA may target any mature rRNA sequence or any pre-rRNA sequence. In one embodiment, primers may target the 5' pre-rRNA leader regions. In one such embodiment, primers for methods of RPA disclosed herein may target the sequences immediately upstream of the mature 5' 16S rRNA terminus because these promoter-proximal regions would be abundant in cells that are actively transcribing pre-rRNA. In another such embodiment, primers for use with RPA may target a spacer sequence downstream of the 16S rRNA gene. In further embodiments, primer pairs may straddle the 5' or 3' mature rRNA terminus, such that amplification requires intact pre-rRNA as templates. Reverse primers for use in the methods for RPA described herein may be designed to recognize semi-conserved regions within the mature rRNA, and forward primers may be designed to recognize species-specific sequences within the pre-rRNA. Alternatively, reverse primers for use in the methods for RPA described herein may be designed to recognize species-specific sequences within the pre-rRNA, and forward primers may be designed to recognize semi-conserved regions within the mature rRNA. Length and composition of primers are not important to the invention, as long as they are designed to specifically amplify pre-rRNA and not mature rRNA or DNA.

In one particular embodiment, primers may be designed to quantify pre-rRNA molecules of *M. avium*. In one such embodiment, with reference to FIG. 7, forward and reverse primers can be designed to generate an amplification product that straddles the 5' mature 16S rRNA terminus, such that successful amplification requires intact pre-16S rRNA as a template. For example, the cDNA synthesis for RT-qPCR may be primed by the mature rRNA sequence 5'-GCCCG-CACGCTCACAGTTAAG-3' (SEQ ID NO: 3). Forward and reverse PCR primers may be 5'-TTGGCCATACCTAG-CACTCC-3' (SEQ ID NO: 1) and 5'-GATTGCCCACGTGT-TACTCA-3' (SEQ ID NO: 2), respectively. The reverse primer may be within the mature rRNA sequence, whereas the forward primer may recognize a site in external transcribed spacer-1 (ETS-1). Examples of primers for use with the methods of RPA are shown in FIG. 7 including sets of forward, reverse, and reverse transcriptase primers, and alternative primers, which may be used with the referenced target microorganisms.

For the methods disclosed herein, the pre-rRNA stimulation ratio values are the ratios of pre-rRNA levels in stimulated samples relative to pre-rRNA levels in control samples. In particular embodiments, methods of RPA disclosed herein include the step of ratiometrically quantifying species-specific pre-rRNA in a sample. In one embodiment, species-specific pre-rRNA is quantified ratiometrically to determine the pre-rRNA stimulation ratio values. In one such embodiment, pre-rRNA stimulation ratio values are the ratios of pre-rRNA levels in a nutritionally stimulated sample relative to a non-nutritionally stimulated control sample, and the pre-rRNA stimulation values are used to determine the presence of viable target cells in a sample. For example, the presence of viable cells is indicated when the pre-rRNA stimulation ratio value is approximately equal to, or greater than, a viability threshold value. In one such embodiment, the viability of targeted cells is indicated by a viability threshold value when the pre-rRNA levels in a nutritionally stimulated aliquot are greater than the pre-rRNA values in non-stimulated control aliquot.

As used herein, the term "viability threshold value" is the calculated ratio of pre-rRNA levels in stimulated samples relative to pre-rRNA levels in control samples that indicates the presences of viable cells in a sample. As disclosed herein, the viability threshold value for a given sample may depend on the target organism, the type of sample, the resolving power of the NAAT, and other conditions that may affect the quantification of pre-rRNA in the sample. In specific embodiments, the viability threshold value for a sample may range from approximately 1 to 100. The choice of a threshold value might depend upon specific assay requirements. For example, a test that requires the highest possible sensitivity for the presence of a pathogen (such as medical device quality control) might use a threshold value of 1. Alternatively, a test that requires specificity for viable cells but not a high degree of analytical sensitivity, such as wastewater treatment monitoring, might use a higher threshold value to minimize the frequency of costly false-positive results.

In one embodiment, RPA may be conducted on samples derived from natural or in vivo sources. For example, the methods for RPA described herein may be conducted on samples derived from tissues or bodily fluids. In one embodiment, a sample may be collected from the tissue, blood or sputum of a human or animal subject. In comparison to tap or lake water, blood and sputum may be nutrient-rich environments. Microorganisms in such natural samples may replicate actively and maintain large pre-rRNA pools. However, the balanced and optimized nutritional conditions of laboratory media are very rare in nature. In natural environments microbial growth is usually limited by the availability of specific nutrients. For example, humans have innate immune mechanisms that limit iron availability in tissues. Because specific nutrients are limiting, microorganisms may divide poorly, if at all, in natural samples such as sputum or whole blood. In this sense natural environments are similar to spent culture media, which contain large amounts of some nutrients but are depleted for others (usually carbon or nitrogen). A natural sample containing microorganisms that are limited for a specific nutrient, be it carbon, nitrogen, oxygen, or a trace element, can undergo a measurable burst of pre-rRNA synthesis when provided with the limiting nutrient under nutritional stimulation.

In one embodiment, samples collected for RPA as disclosed herein may include natural samples comprising spatial variations with regard to nutrient availability and the presence of growth inhibitors and host defenses. For example, tuberculosis bacilli in freshly infected macrophages may replicate at top speed, while growth is likely to be slow in the extracellular matrix or in host cells with very large bacillary burdens. In one such embodiment, for natural samples collected during acute infection in a subject it may be unlikely that all potential target organisms in a sample are provided the optimum nutrient mix to ensure maximum cell growth. As such, target microorganisms in natural samples can be expected to synthesize pre-rRNA and show pre-rRNA upshift when incubated under nutritional stimulation conditions. In one embodiment, methods of RPA as disclosed herein may comprise collecting a natural sample comprising a target microorganism living in a nutrient limited environment. In one such embodiment, the methods of RPA as described herein may include determining the limiting nutrient in the natural sample and then nutritionally stimulating an aliquot of the natural sample with an enriched nutrient media comprising the limiting nutrient. Accordingly, the enriched nutrient media may cause an upshift in the pre-rRNA levels in the target microorganism by providing the limiting nutrient to the target microorganism.

In one particular embodiment, RPA may be conducted for a target organism such as *M. tuberculosis* in a sample derived from a human or animal subject. In one such embodiment, sputum may be collected from a subject suspected of being infected with *M. tuberculosis* or undergoing treatment for *M. tuberculosis*. The sputum samples may be divided into 2 aliquots, one of which may be nutritionally stimulated with enrichment media, such as Middlebrook 7H9 broth, while the other can be held in PBS or water as a control. In one embodiment, nutritional stimulation may proceed for approximately 3-5 hours at 37° C. The bacteria in the stimulated and control aliquots may then be lysed and RT-qPCR may be used to quantify pre-rRNA and calculate pre-rRNA stimulation ratio values. Pre-rRNA stimulation values may be used to determine the presence of viable *M. tuberculosis* in the natural sample. In one such embodiment, the presence of viable *M. tuberculosis* cells is indicated when the pre-rRNA values in the nutritionally stimulated aliquot are greater than the pre-rRNA values in the non-stimulated control aliquot. In similar embodiments, intracellular pathogens of the genera *Chlamydia, Listeria, Legionella*, or others may be detected by RPA using nutritional stimulation with limiting nutrients. Target pathogens do not need to be "culturable" in vitro. For example, an obligate intracellular pathogen such as *Chlamydia trachomatis* can be detected in a vaginal swab by using RPA in which a specific nutrient is provided that was limiting in its natural intracellular environment. The pathogen may not be able to replicate under these conditions, but it can sense the presence of the limiting nutrient and synthesize pre-rRNA in an abortive attempt to replicate, because pre-rRNA synthesis is a very early step in cell growth. Such synthesis would be detectable by RPA.

Well-known manual or automated methods for nucleic acid extraction and quantification may be applied in carrying out the methods of RPA as disclosed herein. In one such embodiment, RPA may include nucleic acid extraction and/or quantification that uses one or more technologies such as nucleic acid chip technology, microarrays, multiplex technology, lab-on-a-chip, lab-on-a-card, microfluidic devices, and other nucleic acid extraction and quantification technologies known by those of skill in the art. As used herein, the term "microfluidic device" is a device that may be used to conduct RPA and may include nucleic acid chip technology, microarrays, multiplex technology, lab-on-a-chip, lab-on-a-card, and related technologies. For example, methods of nucleic acid extraction and analysis are disclosed in U.S. Pat. No. 7,608,399 and U.S. patent application Ser. No. 11/880,790, both of which are incorporated by reference herein.

In one embodiment, the methods of RPA disclosed herein may include using a Nucleic Acid Card for RNA extraction and amplification, followed by ratiometric analysis. An aliquot taken from a sample is nutritionally stimulated while a control aliquot is held in buffer (step A). After brief nutritional stimulation, the cells are lysed (step B) and then loaded onto paired Nucleic Acid Cards. Upon completion of the RNA extraction (step C), eluates are subjected to qPCR. When applied to slow-growing mycobacteria, the total process including nutritional stimulation may take from 6 to 24 hours. Comparatively, *Mycobacterium* culture requires 5-14 days.

In one embodiment, RPA as disclosed herein may include nucleic acid extraction and quantification using a flat-glass or composite card capable of quickly, easily, and reliably isolating DNA and RNA from blood and a variety of other biological samples. In one embodiment, RPA as disclosed herein may be conducted using a device that combines cellular lysis, nucleic acid extraction and purification, and measurement of extracted nucleic acids. In one such embodiment, the device may be a vessel for receiving and processing a biological sample as described herein. In one such embodiment, the methods of RPA disclosed herein may comprise the use of a flow-through glass walled nucleic acid card for extraction of nucleic acids from a sample. In such an embodiment, the card may be used for nucleic acid quantification, DNA or RNA extraction and concentration determination. In an alternative embodiment, the extraction and/or quantification of nucleic acids may be done manually by using pipettes inserted into loading and elution ports located on a nucleic acid card. Alternatively, the extraction and/or quantification of nucleic acids as disclosed herein may be automated by using a fluid handling device or other appropriate devices known by those of skill in the art.

The methods of RPA as disclosed herein may include a pre-screening process, such as an immunoseparation or immunoscreening process, to improve the specificity of RPA. In one embodiment, RPA may comprise a step in which one or more target microorganisms of interest may be identified or captured on beads or other particles that are coated with antibodies or other probes or peptides that bind specifically to the target microorganisms. In one such embodiment, target microorganisms identified by antibodies or probes may be subjected to RPA as disclosed herein. For example, target microorganisms identified by a preliminary immunoseparation process may be divided into two or more separate aliquots wherein one aliquot is nutritionally stimulated and another aliquot is reserved as a non-nutritionally stimulated control aliquot. Pre-rRNA replenishment in nutritionally stimulated samples relative to control samples can then be quantified as described herein. In one embodiment, an immunoseparation process as described herein may be used to isolate a specific strain or population of a target microorganism. For example, a method of RPA as disclosed herein may comprise an immunoseparation step wherein a specific strain or isolate within a population of target microorganisms may be identified. In one particular example, a method of RPA as disclosed herein may comprise an immunoseparation step wherein a specific *E. coli* strain such as *E. coli* O157 is separated from other microorganisms of the same species.

In one embodiment, RPA as disclosed herein may be used to improve the sensitivity of detection of target microorganisms. For example, RPA may be used to confirm the presence of viable target microorganisms in conjunction with another test. As a dynamic measurement of a cellular activity, RPA as disclosed herein offers greater confidence in borderline signals than does static DNA detection. This may improve the overall sensitivity, reliability, and robustness of nucleic acid amplification tests for microorganisms in a sample. The improved biological sensitivity stems from the dynamic nature of RPA. An analogy would be the observation of animals in a forest, in that a moving animal is much easier to spot than a stationary one. The pre-rRNA synthesis seen in RPA is a type of bacterial "movement" that is reliably induced by nutritional stimulation.

Furthermore, RPA has additional advantages over traditional NAATs. Most reverse transcriptase quantitative-PCR (RT-qPCR) protocols have 3 steps: DNAse digestion to remove genomic DNA that might interfere with RNA quantification; reverse transcriptase (RT) to convert RNA to cDNA; and finally qPCR to quantify the cDNA. In RPA the DNAse digestion step is not necessary, because genomic DNA in bacterial cells is outnumbered by pre-rRNA by 1-3 orders of magnitude. Genomic DNA is also expected to be found in similar quantities in stimulated and control aliquots. As a result, genomic DNA causes very little background signal and does not interfere with the ratiometric analysis.

In one embodiment, RPA may be used to improve the confidence in the results of a primary analysis when the primary analysis gives results that are inconclusive, borderline, or difficult to interpret. For example, generally, RT-qPCR with cycle threshold (Ct) values of <30 (i.e. positive results after fewer than ~30 amplification cycles) are unambiguously positive. However, Ct values >30 are borderline and can be difficult to interpret. Such signals can result from sample contamination or even from background noise. In one embodiment, RPA may be used to confirm the results of a RT-qPCR test for the presence of microbial cells when Ct values are >30. When repeated measurements are made and nutritionally stimulated aliquots exhibit RT-qPCR signal that are consistently stronger than control aliquots, then this result most likely reflects the presence of viable cells. Background noise, DNA contamination, or other causes of borderline positive results would be highly unlikely to cause such results. Therefore, in addition to improving specificity for viable microbial cells, RPA can significantly improve the functional sensitivity of NAAT for microbial cells. Other examples of NAATs may include non-ratiometric rRNA amplification (mature or precursor) and non-ratiometric rRNA detection by direct hybridization.

In addition to Ct values, other quantitative or semi-quantitative NAAT test read-outs can be used with RPA. Examples include gel electrophoresis results, fluorescent or colorimetric signals, thermal read-outs, melt curves, and nucleic acid probe hybridization-based read-outs such as line probe assays or nucleic acid lateral flow (NALF). In all cases, RPA can improve specificity for viable cells as well as functional sensitivity for detection of microbial cells present in small numbers.

In one embodiment, RPA may be used to increase the sensitivity of a primary NAAT, such as a DNA detection assay designed to identify the presence of microorganisms in a sample. In one such embodiment, a genomic DNA detection assay of a sample may be performed concurrently with RPA, or followed by RPA, for the same sample to detect the presence of viable target microorganisms. In another embodiment, RPA may be used to overcome background noise or environmental DNA contamination that may make it difficult to interpret borderline results generated by methods for detecting target microorganisms.

EXAMPLES

The Examples that follow are offered for illustrative purposes only and are not intended to limit the scope of the compositions and methods described herein in any way. It is to be understood that the disclosed compositions and methods are not limited to the particular methodologies, protocols, and reagents described herein. In each instance, unless otherwise specified, standard materials and methods were used in carrying out the work described in the Examples provided. All patent and literature references cited in the present specification are hereby incorporated by reference in their entirety.

The practice of the present invention employs, unless otherwise indicated, conventional techniques of chemistry, molecular biology, microbiology, recombinant DNA, genetics, immunology, cell biology, cell culture and transgenic biology, which are within the skill of the art. (See, e.g., Real-Time PCR in Microbiology: From Diagnosis to Characterization (I. M. Makay ed. 2007); Nolan, T., et al. (2006) Quantification of mRNA using real-time RT-PCR. *Nature Protocols* 1, 1559-1582; Maniatis, T., et al. (1982) Molecular Cloning: A Laboratory Manual (Cold Spring Harbor Laboratory, Cold Spring Harbor, N.Y.); Sambrook, J., et al. (2001) Molecular Cloning: A Laboratory Manual, 2$^{nd}$ Ed. (Cold Spring Harbor Laboratory, Cold Spring Harbor, N.Y.); Ausubel, F. M., et al. (1992) Current Protocols in Molecular Biology, (J. Wiley and Sons, NY); Glover, D. (1985) DNA Cloning, I and II (Oxford Press); Anand, R. (1992) Techniques for the Analysis of Complex Genomes, (Academic Press); Guthrie, G. and Fink, G. R. (1991) Guide to Yeast Genetics and Molecular Biology (Academic Press); Harlow and Lane (1988) Antibodies: A Laboratory Manual (Cold Spring Harbor Laboratory, Cold Spring Harbor, N.Y.); Jakoby, W. B. and Pastan, I. H. (eds.) (1979) Cell Culture. Methods in Enzymology, Vol. 58 (Academic Press, Inc., Harcourt Brace Jovanovich (NY); Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Hogan et al. (eds) (1994) Manipulating the Mouse Embryo; A Laboratory Manual, 2$^{nd}$ Edition, Cold Spring Harbor Laboratory Press, Cold Spring Harbor, N.Y.). The practice of the present invention employs, unless otherwise indicated, conventional techniques of chemistry, molecular biology, microbiology, recombinant DNA, genetics, and immunology. (See, e.g., Maniatis et al., 1982; Sambrook et al., 2001; Ausubel et al., 1992; Glover, 1985; Anand, 1992; Guthrie and Fink, 1991).

Nothing herein is to be construed as an admission that the subject matter taught herein is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Example 1

Design of Pre-rRNA-Based Cell Viability Tests

Pre-rRNA pools are rapidly replenished by bacteria that sense new nutrients in their environments. As shown in FIG. 1, pre-16S rRNA pools are replenished in *E. coli* after a nutritional upshift of stationary phase cells. With continued reference to FIG. 1, overnight cultures of *E. coli* were diluted 20-fold into fresh LB broth at time zero (arrow). At time points before and after dilution, optical densities were recorded, and samples were analyzed for pre-rRNA and mature 16S rRNA content by chemiluminescent sandwich hybridization assays. Open circles, culture OD600 (right axis); open triangles, pre-16S rRNA per OD600 (left axis); filled triangles, mature 16S rRNA per OD600. Means and standard deviations of three parallel cultures are shown in FIG. 1.

Figure 2:
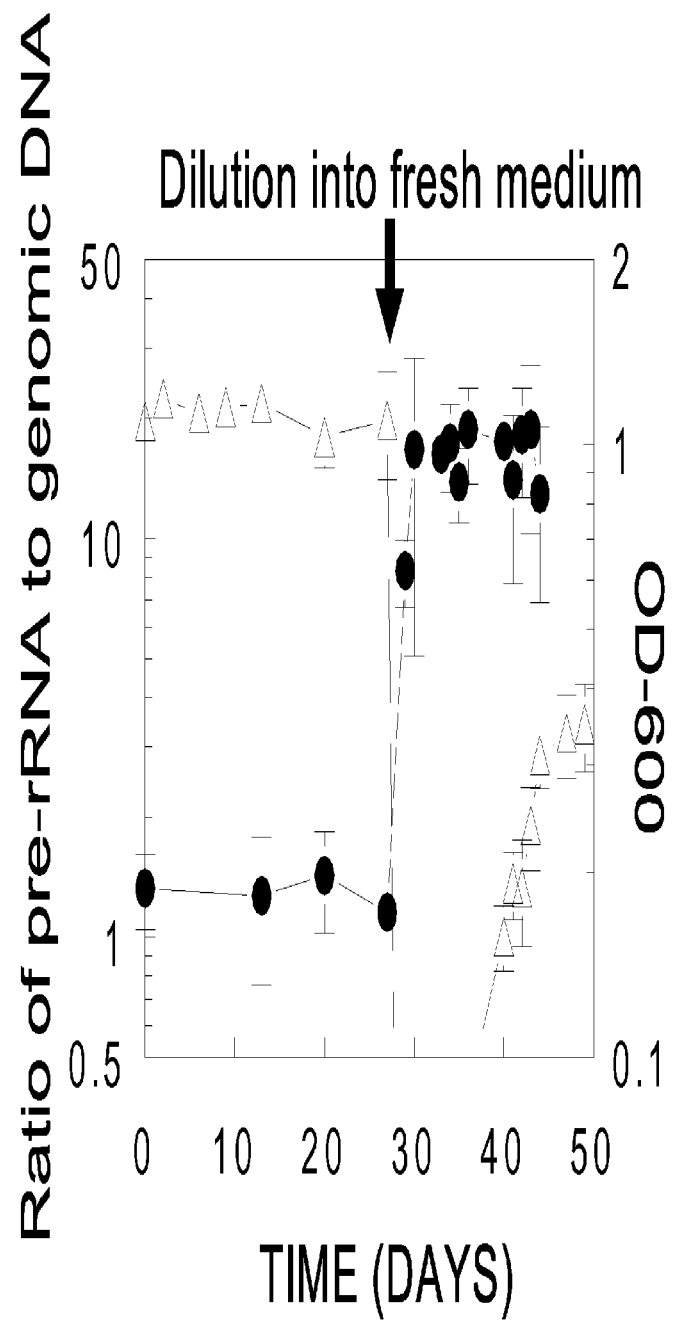
FIG. 2 shows pre-16S rRNA pool upon nutritional stimulation of stationary phase *M. bovis* BCG.

In contrast to *E. coli*, which divides and doubles every 30 min and has high rRNA copy number, *Mycobacterium bovis* BCG doubles every ~24 hours and has fewer rRNA copies. Nonetheless, pre-rRNA replenishment is clearly visible within one doubling time of nutritional upshift in this organism. FIG. 2 illustrates this in an experiment conducted on *M. bovis* BCG in which a slot blot hybridization assay was used to detect pre-rRNA (closed circles). With continued reference to FIG. 2, stationary phase *M. bovis* BCG cells were diluted into fresh 7H10 broth at the time indicated by the arrow. Pre-rRNA copy number and cell density were tracked before and after nutritional stimulation. Closed circles show the pre-rRNA to genomic DNA ratio. Open triangles show the OD600 of the *M. bovis* culture. Direct detection without amplification was possible because pre-rRNAs are abundant in bacterial cells, accounting for 4%-20% of total rRNA. As a result, the sensitivity of pre-rRNA detection exceeds that of genomic DNA detection.

Example 2

Ratiometric Pre-rRNA Analysis

RPA tests were developed for two bacterial pathogens suspected of causing human disease acquired from drinking water. The model species were the rapidly growing gram negative bacillus *Aeromonas hydrophila* and the slowly growing actinomycete *Mycobacterium avium*. For both species, 5' pre-rRNA leader regions (the sequences immediately upstream of the mature 5' 16S rRNA terminus) were targeted on the assumption that these promoter-proximal regions would be abundant in cells that are actively transcribing pre-rRNA. Primer pairs straddled the 5' mature rRNA terminus, such that amplification required intact pre-rRNA as templates. Reverse primers recognized semi-conserved regions within the mature rRNA. Forward primers recognized species-specific sequences within the 5' leader.

M. avium forward and reverse primers were designed to generate a predicted 237 bp amplification product that straddled the 5' mature 16S rRNA terminus, such that successful amplification required intact pre-16S rRNA as a template. The cDNA synthesis was primed by the mature rRNA sequence 5'-GCCCGCACGCTCACAGTTAAG-3' (SEQ ID NO: 3). Forward and reverse PCR primers were 5'-TTGGC-CATACCTAGCACTCC-3' (SEQ ID NO: 1) and 5'-GAT-TGCCCACGTGTTACTCA-3' (SEQ ID NO: 2), respectively. The reverse primer was within the mature rRNA sequence, whereas the forward primer recognized a site in ETS-1. Consistent with the species specificity predicted from BLAST analysis, PCR with gel electrophoresis consistently yielded products of the expected sizes when applied to nucleic acid from 15 clinical isolates of M. avium and 4 clinical isolates of M. intracellulare. These two closely-related species comprise the clinically relevant grouping known as the M. avium complex (MAC). No products were observed when the reactions were applied to M. tuberculosis, M. smegmatis, M. terrae, M. gastri, M. nonchromogenicum, M. phlei, and M. vaccae (data not shown). These observations illustrate the useful phylogenetic specificity of pre-rRNA analysis.

A. hydrophila forward and reverse primers generated a predicted 189 bp amplification product. The cDNA synthesis was primed by the mature rRNA sequence 5'-CTACAA-GACTCTAGCTGGACAGT-3' (SEQ ID NO: 6). Forward and reverse PCR primers were 5'-ATTGAGCCGCCTTAA-CAGG-3' (SEQ ID NO: 4) and 5'-AACTGTTATCCCCCTC-GAC-3' (SEQ ID NO: 5), respectively. BLAST analysis conducted against the NCBI non-redundant database found no matches with the forward primer other than A. hydrophilia. The closely related species A. salmonicida A449 did not have a homologous sequence.

To assess the time course of pre-rRNA replenishment upon nutritional stimulation, early stationary-phase A. hydrophila ATCC 7966 cells were washed, resuspended in autoclaved tap water (ATW), and incubated for 7 days with aeration at 28° C. Early stationary-phase cells of MAH strain HMC02 were washed, resuspended in ATW, and then incubated for 14 days with aeration at 37° C. These conditions were designed to drain pre-rRNA pools in simulated water supply environments. To conduct RPA, water-starved bacteria were divided into two aliquots and centrifuged. One pellet was resuspended in culture media (nutritional stimulation), and the other in ATW (control). Final cell densities were approximately $10^6$ cfu/mL. Nutrient Broth was used for nutritional stimulation of A. hydrophila, and Middlebrook 7H9 medium with 10% ADC supplement was used for MAH. After incubation for varying periods of time, cells were lysed by high-energy bead beating, RNA was isolated by acidified phenol-chloroform, and pre-rRNA was measured by RT-qPCR. The ratios of RT-qPCR values in nutritionally stimulated and control samples were calculated following normalization to genomic DNA standard curves. Pre-rRNA stimulation was very rapid in both organisms. Approximately 15 minutes of nutritional stimulation was adequate for consistent pre-rRNA upshift in A. hydrophila. Approximately 4 hours was required for maximal pre-rRNA stimulation in M. avium, a slow-growing organism with a generation time of >20 hours. For both organisms these time periods are <1 generation time.

Figure 3:
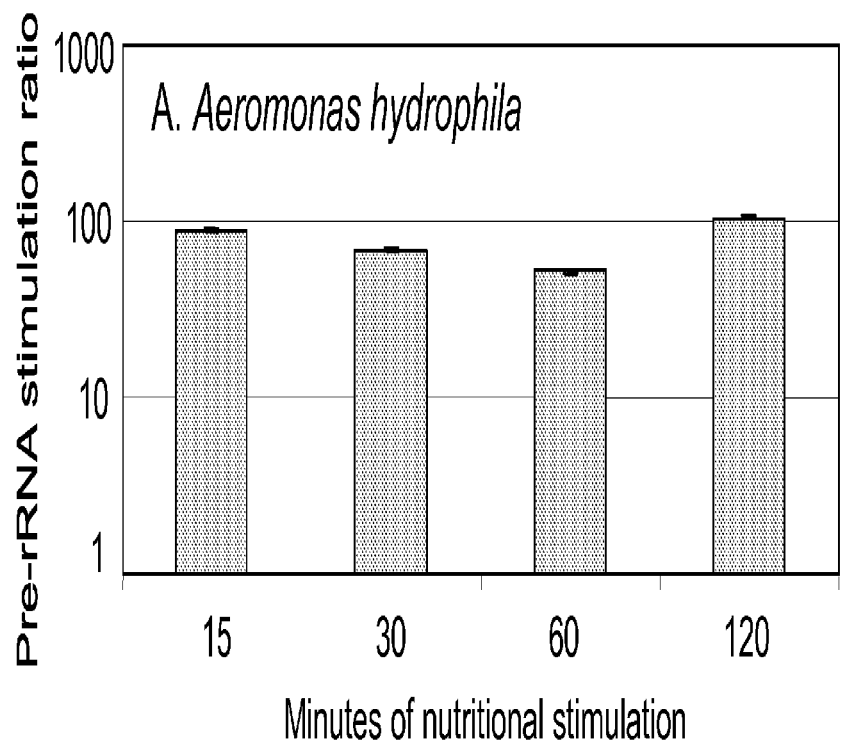
FIGS. 3A and 3B show the timecourse of nutritional stimulation of pre-rRNA in water-starved *A. hydrophila* (A) and *M. avium* strain 104 (B) cells.
Figure 3:
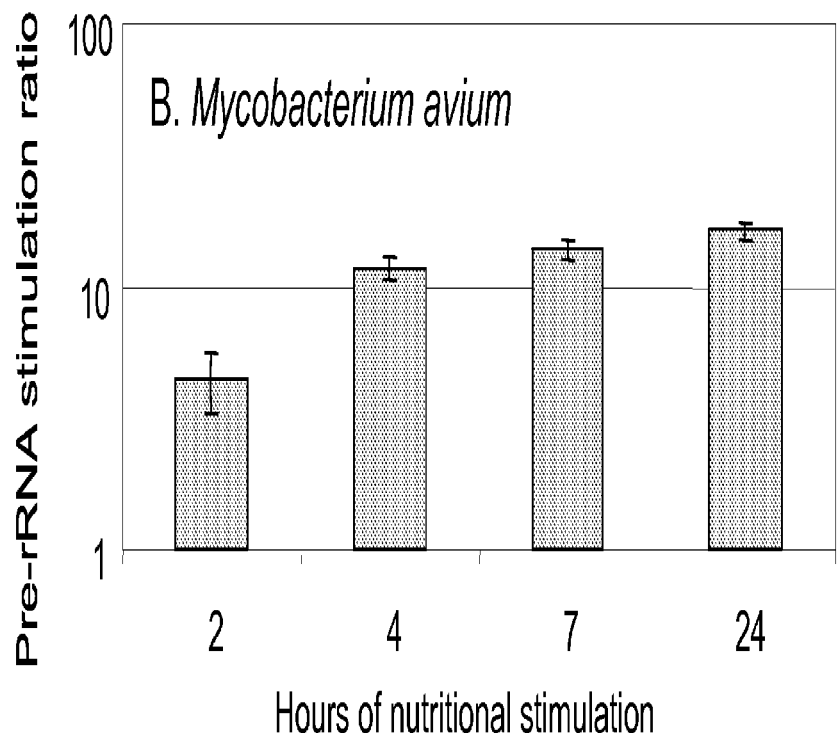

FIG. 3 shows the timecourse of nutritional stimulation of pre-rRNA in water-starved A. hydrophila (A) and M. avium strain 104 (B) cells. Pre-rRNA stimulation ratio values are the ratios of pre-rRNA in stimulated samples relative to control samples, measured by RT-qPCR. Values are means and SD of >2 experiments per time point. To conduct RT-qPCR on extracted RNA, complementary DNA (cDNA) was first generated using the Superscript III system (Invitrogen Corp., Carlsbad, Calif.) and cleaned using a Qiagen PCR purification kit (Cat#28104, Qiagen Inc., Valencia, Calif.). Amplification of cDNA was performed using the Applied Biosystems (ABI) Power SYBR Green mix (Applied Biosystems Inc., Foster City, Calif.). Reactions were conducted in triplicate at two different dilutions to assure quantitative read-outs. Amplifications were run in 96-well plates on an ABI Prism RT-7500 as follows: 10 minutes 95° C., 40 cycles of (15 s 95° C., 30 s 60° C., 30 s 72° C.) using '9600 emulation.' ABI's SDS software was used to set Ct threshold values.

Example 3

Correlation Between Pre-rRNA Stimulation Ratio and Cell Viability

To assess the specificity of RPA for viable cells, sodium hypochlorite treatment was used to generate A. hydrophila cell suspensions with varying ratios of viable and inactivated cells. The ratios were quantified by viable plating after chlorine exposure, and were expressed as percent viability relative to the input density of approximately $1 \times 10^6$ cfu/mL. To conduct RPA on the chlorine-treated and -untreated cell suspensions, paired aliquots were centrifuged and cell pellets were resuspended in water (control sample) or nutrient broth (stimulated sample). After 1 hour of nutritional stimulation, pre-rRNA stimulation ratios were determined. In some experiments, genomic DNA in stimulated and control samples was also quantified by qPCR. This allowed assessment of the specificity of RPA to viable cells, in comparison to the specificity seen with traditional qPCR of DNA.

Table 1 shows results of two experiments in which genomic DNA as well as pre-rRNA were measured. In the first experiment, samples with percent viabilities of 96.3%, 26.9%, and 0.02% exhibited pre-rRNA stimulation ratios values of ≥3±1 SD. Samples with no detectable viable cells (0% viability) exhibited pre-rRNA stimulation ratios that were not statistically greater than 1.0. Therefore, RPA showed significant pre-rRNA stimulation ration values in a sample where up to approximately 99.98% of the target microorganisms were dead. In contrast, qPCR detection of A. hydrophila genomic DNA was strongly positive in all samples, regardless of cell viability. Moreover, there was no difference between DNA signals in nutritionally stimulated and control aliquots (not shown). Similar results were seen in the second experiment (Table 1). This example illustrates the remarkable sensitivity of RPA for viable cells, even when outnumbered by inactivated cells by factors of 5000-fold or more, as in the sample in Experiment 1 that was treated with 2 mg/l hypochlorite.

TABLE 1

| Hypochlorite (mg/l) | Final cfu/mL | Percent viability[1] | Pre-rRNA stimulation ratio[2] | Genomic DNA copies (millions) |
|---|---|---|---|---|
| Experiment 1 | | | | |
| 0 | 963000 | 96.3 | 3.0 ± 0.2 | 1.4 ± 0.4 |
| 1 | 279000 | 27.9 | 17.2 ± 3.6 | 3.8 ± 0.5 |
| 2 | 190 | 0.02 | 73.0 ± 54.2 | 4.0 ± 0 |
| 3 | 0 | 0 | 0.6 ± 1.0 | 3.8 ± 0.5 |
| 4 | 0 | 0 | 0.04 ± 0.1 | 5.4 ± 0.6 |

TABLE 1-continued

| Hypochlorite (mg/l) | Final cfu/mL | Percent viability[1] | Pre-rRNA stimulation ratio[2] | Genomic DNA copies (millions) |
|---|---|---|---|---|
| Experiment 2 | | | | |
| 0 | 774000 | 77.4 | 39.4 ± 17.0 | 0.5 ± 0.1 |
| 1 | 846000 | 84.6 | 17.44 ± 5.4 | 2.2 ± 0.5 |
| 1.5 | 186000 | 18.6 | 16.47 ± 6.6 | 2.7 ± 0.1 |
| 2 | 0 | 0 | 1.28 ± 0.4 | 2.2 ± 0.04 |

[1]Normalized to estimated 1 × 10⁶ input bacteria.
[2]Mean ± SD of 3 replicate samples.

Figure 4:
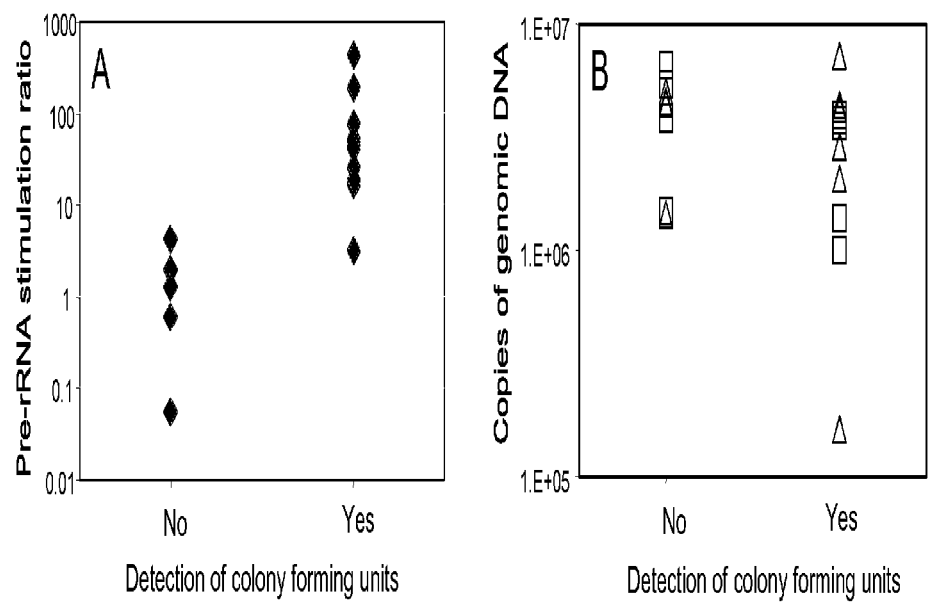
FIGS. 4A and 4B show the correlation between the presence of viable *A. hydrophila* cells and pre-rRNA stimulation ratio (A) or genomic DNA quantified by qPCR (B) in hypochlorite treated laboratory suspensions.

In four experiments using the protocol in Table 1, RPA was applied to a total of 18 chlorine-treated and untreated samples with varying percent viabilities. Pre-rRNA stimulation ratios observed in samples with no detectable colony forming units were significantly lower (p=0.0026 by the Mann-Whitney U test) than those observed in samples with detectable colony forming units (FIG. 4A). There was some overlap between the two groups, however the overlap was significantly less than that seen when genomic DNA was quantified by qPCR in either stimulated or non-stimulated samples (FIG. 4B). There was no significant correlation between viability and DNA stimulation ratios. More specifically, FIG. 4 shows the correlation between the presence of viable *A. hydrophila* cells and pre-rRNA stimulation ratio (A) or genomic DNA quantified by qPCR (B) in hypochlorite treated laboratory suspensions. Pre-rRNA stimulation ratio values (A) are the ratios of pre-rRNA in stimulated samples relative to control samples, measured by RT-qPCR. Values are means of 3 measurements per sample. Genomic DNA copies (B) were quantified by qPCR normalized to a genomic DNA standard curve. DNA was measured in nutritionally stimulated samples (open squares) as well as non-stimulated samples (open triangles).

Example 4

Field Testing of an RPA Assay

As a common inhabitant of surface waters, *A. hydrophila* was a convenient model for field testing RPA. Samples were collected from fresh and salt water sites in Seattle, Wash. A portion of each sample was autoclaved to generate an inactivated control. Autoclaved and non-autoclaved samples (300 mL each) were concentrated by filtration. After re-suspension, aliquots were diluted two-fold in 2× nutrient broth (stimulated sample) or water (control). After 1 hour of incubation, bacteria and particulates were concentrated by centrifugation and then *A. hydrophila* pre-rRNA in the pellets was measured by RT-qPCR. Viable counts of *A. hydrophila* in the samples were determined by viable plating following standard methods.

TABLE 2

| Site | Description | *A. hydrophila* viable counts (mean cfu per mL ± SD) | Pre-rRNA (mean ratio stimulated/control ± SD)[1] |
|---|---|---|---|
| A1 | Fresh water | 798 | 4.8 ± 1.4 |
| A2 | Fresh water | 280 | 9.5 ± 5.9 |
| B | Salt water | 6 | No pre-rRNA detected |
| C | Fresh water | 760 | 39.8 ± 12.8 |

[1]Means and standard deviations of ≥4 measurements per sample.

In total, 3 fresh water samples and 1 salt water sample were analyzed. The fresh water samples yielded viable counts of *A. hydrophila* ranging from 280 to 798 cfu/mL. All of them exhibited positive RPA signals (Table 2). All autoclaved samples yielded no cfu and no *A. hydrophila* pre-rRNA was detected in these samples. The salt water sample had 6 cfu/mL *A. hydrophila*, however no *A. hydrophila* pre-rRNA was detected in either stimulated or non-stimulated samples, with or without autoclaving.

The results support the use of RPA as a means to specifically detect viable microorganisms in environmental samples. The RPA methods may be used to eliminate false positive results seen in samples containing only dead bacterial cells and DNA. The use of RPA can also reduce false positives caused by laboratory contamination of samples or PCR reagents. Furthermore, RPA is robust and built upon a physiological feature of all bacteria and is useful in food and water safety analysis, either by itself or as an adjunct to other tools.

Example 5

Biological Sensitivity of RPA

Figure 5:
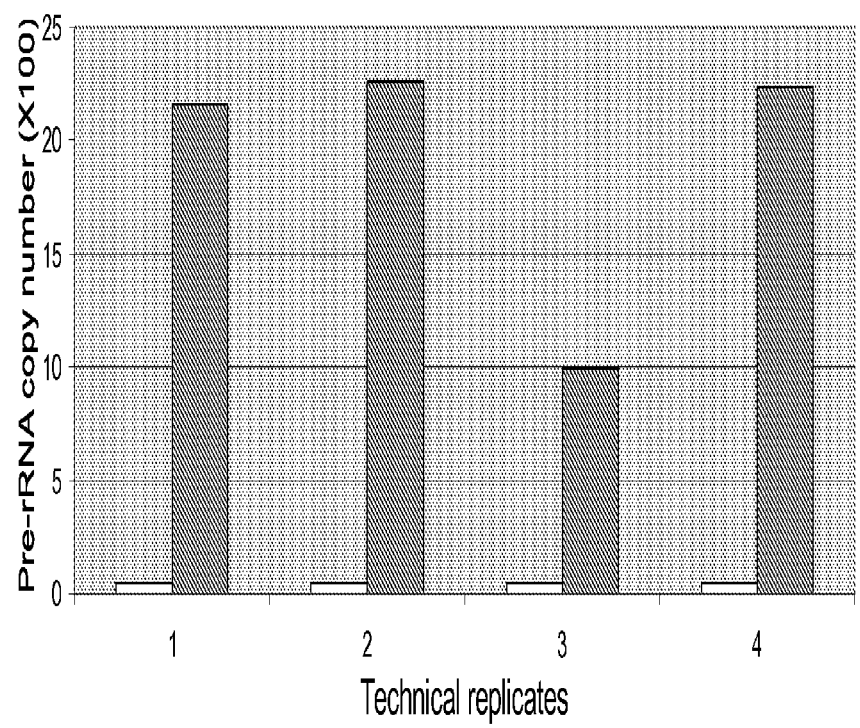
FIG. 5 shows the results of multiple RT-qPCR reactions conducted on paired stimulated and control aliquots derived from a single fresh water lake sample.

RPA may be used to improve assay sensitivity relative to genomic DNA detection. FIG. 5 shows the results of multiple RT-qPCR reactions conducted on paired stimulated and control aliquots derived from a single fresh water lake sample (sample A2 from Table 2) that contained 280 cfu/mL viable *A. hydrophila*. With continued reference to FIG. 5, a sample from Lake Union, Seattle, Wash. was divided into two aliquots, one of which was stimulated with nutrient broth (dark bars) and the other resuspended in ATW (light bars) as a control. The results shown in FIG. 5 are expressed as approximate pre-rRNA copies per mL of sample calculated by comparing cycle threshold (Ct) values to a genomic DNA standard curve. In each of these technical replicates, pre-rRNA signals in stimulated samples exceeded those of control samples by substantial margins.

The Ct values in Table 2 were all in the range of 32 to 43, i.e. signals were borderline and weak. This was most likely due to PCR inhibitors that are common in concentrated surface water samples. Despite these limitations, the results were unambiguously positive, because the consistent upshift in pre-rRNA signal in stimulated samples lent confidence to the conclusion that viable *A. hydrophila* cells were present.

The invention claimed is:

1. A method of detecting whether at least one target prokaryotic microorganism in a sample is viable, the method comprising:
   collecting a sample;
   nutritionally stimulating and incubating a first aliquot of the sample at one or more temperatures for a time period, thereby producing a nutritionally stimulated first aliquot, wherein the time period is less than the time for the at least one target prokaryotic microorganism to grow for one generation;
   maintaining and incubating a second aliquot of the sample under non-nutritionally stimulating control conditions at the one or more temperatures for the time period, thereby producing a non-nutritionally stimulated second aliquot, wherein the first aliquot and the second aliquot are equal aliquots;
   comparing the level of at least one target pre-rRNA from the at least one target prokaryotic microorganism from the nutritionally stimulated first aliquot with the level of the at least one target pre-rRNA from the at least one target prokaryotic microorganism in the non-nutritionally stimulated second aliquot;

wherein when the ratio of the level of the at least one target pre-rRNA in the nutritionally stimulated first aliquot to the level of the at least one target pre-rRNA in the non-nutritionally stimulated second aliquot is greater than 1, the at least one target prokaryotic microorganism in the sample is viable, and when the ratio is not greater than 1, no viable target prokaryotic microorganism is detected in the sample.

2. The method of claim 1, further comprising extracting RNA from the nutritionally stimulated first aliquot and extracting RNA from the non-nutritionally stimulated second aliquot; and quantifying the level of the at least one target pre-rRNA in the nutritionally stimulated first aliquot and quantifying the level of the at least one target pre-rRNA in the non-nutritionally stimulated second aliquot.

3. The method of claim 2, wherein said extracting RNA from the nutritionally stimulated first aliquot and said extracting RNA from the non-nutritionally stimulated second aliquot and said quantifying the level of the at least one target pre-rRNA in the nutritionally stimulated first aliquot and said quantifying the level of the at least one target pre-rRNA in the non-nutritionally stimulated second aliquot comprises the use of a microfluidic device.

4. A method for determining whether at least one target prokaryotic microorganism in a sample is viable, the method comprising:

dividing the sample into at least a first aliquot and a second aliquot, wherein the first aliquot and the second aliquot are equal aliquots;

nutritionally stimulating and incubating the first aliquot of the sample at one or more temperatures for a time period, thereby producing a nutritionally stimulated first aliquot, wherein the time period is less than the time for the at least one target prokaryotic microorganism to grow for one generation;

maintaining and incubating the second aliquot of the sample under non-nutritionally stimulating control conditions at the one or more temperatures for the time period, thereby producing a non-nutritionally stimulated second aliquot;

extracting RNA from the nutritionally stimulated first aliquot and extracting RNA from the non-nutritionally stimulated second aliquot;

quantifying the level of at least one target pre-rRNA of the at least one target prokaryotic microorganism from the nutritionally stimulated first aliquot;

quantifying the level of the at least one target pre-rRNA of the at least one target prokaryotic microorganism from the non-nutritionally stimulated second aliquot;

comparing the level of the at least one target pre-rRNA from the at least one target prokaryotic microorganism in the nutritionally stimulated first aliquot with the level of the at least one target pre-rRNA from the at least one target prokaryotic microorganism in the non-nutritionally stimulated second aliquot;

wherein when the ratio of the level of the at least one target pre-rRNA in the nutritionally stimulated first aliquot to the level of the at least one target pre-rRNA in the non-nutritionally stimulated second aliquot is greater than 1, the at least one target prokaryotic microorganism in the sample is viable, and when the ratio is not greater than 1, no viable target prokaryotic microorganism is detected in the sample.

5. The method of claim 1, further comprising an immunoseparation process wherein the sample is screened for the presence of a particular isolate of the at least one target prokaryotic microorganism in the sample.

6. The method of claim 5, wherein the immunoseparation process comprises screening the sample for the presence of *E. coli* 0157.

7. The method of claim 1, wherein the at least one target prokaryotic microorganism is a member of a genera of microorganisms selected from the group consisting of *Acinetobacter, Actinobacillus, Aeromonas, Arcobacter, Bacteroides, Bordetella, Borrelia, Brucella, Burkholderia, Campylobacter, Citrobacter, Cronobacter; Edwardsiella, Enterobacter; Escherichia, Eubacterium, Francisella Fusobacterium, Haemophilus, Helicobacter, Klebsiella, Legionella, Leptospira, Moraxella, Morganella, Neisseria, Pasteurella, Plesiomonas, Porphyromonas, Prevotella, Proteus, Providencia, Pseudomonas, Salmonella, Serratia, Shigella, Stenotrophomonas, Treponema, Veillonella, Vibrio, Yersinia, Actinomyces, Bacillus, Bifidobacterium, Clostridium, Corynebacterium, Enterococcus, Lactobacillus, Listeria, Micrococcus, Mobiluncus, Mycobacterium, Nocardia, Peptostreptococcus, Propionibacterium, Rhodococcus, Staphylococcus, Streptococcus,* and *Streptomyces.*

8. The method of claim 1, wherein the at least one target prokaryotic microorganism is a *Mycobacterium* species.

9. The method of claim 1, wherein the at least one target prokaryotic microorganism is *Aeromonas hydrophila.*

10. The method of claim 1, wherein the at least one target prokaryotic microorganism is at least one of *Chlamydia trachomatis, Legionella pneumonia, Listeria monocytogenes, Campylobacter jejuni, Clostridium difficile, Bacillus anthracis, Francisella tularensis, Rickettsia prowasekii, Rickettsia typhi,* and *Helicobacter pylori.*

11. The method of claim 1, wherein said nutritionally stimulating and incubating the first aliquot comprises enriching the first aliquot of the sample with limited nutrients to encourage an upshift in the production of the at least one target pre-rRNA in the at least one target prokaryotic microorganism.

12. The method of claim 1, wherein the method can be used when the percentage of the at least one target prokaryotic microorganism that is viable in the sample is at least one of approximately 0.01%, 0.02%, 0.03%, 0.04%, 0.05%, 0.1%, 0.5%, 1.0%, 2.0%, 3.0%, 4.0%, 5.0%, 10%, 15%, 20%, 25%, 30%, 35%, 40%, 45%, 50%, 55%, 60%, 65%, 70%, 75%, 80%, 85%, 90%, and 95%.

13. The method of claim 4, wherein the dividing step is performed concurrently with a nucleic acid amplification test.

14. The method of claim 4, wherein the dividing step is performed after completion of a nucleic acid amplification test.

15. The method of claim 13 or 14, wherein the nucleic acid amplification test is a DNA amplification test.

16. The method of claim 4, wherein the method can be used when the percentage of the at least one target prokaryotic microorganism that is viable in the sample is at least one of approximately 0.01%, 0.02%, 0.03%, 0.04%, 0.05%, 0.1%, 0.5%, 1.0%, 2.0%, 3.0%, 4.0%, 5.0%, 10%, 15%, 20%, 25%, 30%, 35%, 40%, 45%, 50%, 55%, 60%, 65%, 70%, 75%, 80%, 85%, 90%, and 95%.

17. The method of claim 4, wherein said extracting RNA from the nutritionally stimulated first aliquot and said extracting RNA from the non-nutritionally stimulated second aliquot and said quantifying the level of the at least one target pre-rRNA from the nutritionally stimulated first aliquot and said quantifying the level of the at least one target pre-rRNA from the non-nutritionally stimulated second aliquot comprises the use of a microfluidic device.

18. The method of claim 4, further comprising an immunoseparation process wherein the sample is screened for the presence of a particular isolate of the at least one target prokaryotic microorganism in the sample.

19. The method of claim 4, wherein the at least one target prokaryotic microorganism is a member of a genera of microorganisms selected from the group consisting of *Acinetobacter Actinobacillus, Aeromonas, Arcobacter Bacteroides, Bordetella, Borrelia, Brucella, Burkholderia, Campylobacter, Citrobacter, Cronobacter, Edwardsiella, Enterobacter, Escherichia, Eubacterium, Francisella, Fusobacterium, Haemophilus, Helicobacter, Klebsiella, Legionella, Leptospira, Moraxella, Morganella, Neisseria, Pasteurella, Plesiomonas, Porphytomonas, Prevotella, Proteus, Providencia, Pseudomonas, Salmonella, Serratia, Shigella, Stenotrophomonas, Treponema, Veillonella, Vibrio, Yersinia, Actinomyces, Bacillus, Bifidobacterium, Clostridium, Corynebacterium, Enterococcus, Lactobacillus, Listeria, Micrococcus, Mobiluncus, Mycobacterium, Nocardia, Peptostreptococcus, Propionibacterium, Rhodococcus, Staphylococcus, Streptococcus, and Streptomyces*.

20. The method of claim 4, wherein the at least one target prokaryotic microorganism is a *Mycobacterium* species.

21. The method of claim 4, wherein the at least one target prokaryotic microorganism is *Aeromonas hydrophila*.

22. The method of claim 4, wherein the at least one target prokaryotic microorganism is at least one of *Chlamydia trachomatis, Legionella pneumonia, Listeria monocytogenes, Campylobacter jejuni, Clostridium difficile, Bacillus anthracis, Francisella tularensis, Rickettsia prowasekii, Rickettsia typhi*, and *Helicobacter pylori*.

23. The method of claim 4, wherein said nutritionally stimulating and incubating the first aliquot comprises enriching the first aliquot with limited nutrients to encourage an upshift in the production of the at least one target pre-rRNA in the at least one target prokaryotic microorganism.

* * * * *